US010881882B1

(12) United States Patent
Schwarz et al.

(10) Patent No.: US 10,881,882 B1
(45) Date of Patent: Jan. 5, 2021

(54) METHODS AND DEVICES FOR TISSUE TREATMENT

(71) Applicant: BTL Medical Technologies S.R.O., Prague (CZ)

(72) Inventors: Tomáš Schwarz, Prague (CZ); Daniel Mališ, Prague (CZ)

(73) Assignee: BTL MEDICAL TECHNOLOGIES S.R.O., Prague (CZ)

(*) Notice: Subject to any disclaimer, the term of this patent is extended or adjusted under 35 U.S.C. 154(b) by 0 days.

(21) Appl. No.: 16/282,597

(22) Filed: Feb. 22, 2019

Related U.S. Application Data

(60) Provisional application No. 62/783,431, filed on Dec. 21, 2018.

(51) Int. Cl.
| | | |
|---|---|---|
| *A61N 2/00* | (2006.01) |
| *A61H 23/00* | (2006.01) |
| *A61B 18/18* | (2006.01) |
| *A61N 1/32* | (2006.01) |
| *A61N 7/02* | (2006.01) |
| *A61N 1/40* | (2006.01) |
| *A61N 1/44* | (2006.01) |
| *A61N 5/06* | (2006.01) |
| *A61N 7/00* | (2006.01) |

(52) U.S. Cl.
CPC ............ *A61N 7/02* (2013.01); *A61N 1/403* (2013.01); *A61N 1/44* (2013.01); *A61N 2/004* (2013.01); *A61N 5/0625* (2013.01); *A61N 2007/0034* (2013.01)

(58) Field of Classification Search
CPC .... A61K 2300/00; A61K 38/05; A61K 38/06; A61K 38/07; A61N 7/00; A61N 2/02; A61N 5/0616; A61N 2007/0034; A61N 2/004
See application file for complete search history.

(56) References Cited

U.S. PATENT DOCUMENTS

| | | | | |
|---|---|---|---|---|
| 5,413,550 A | * | 5/1995 | Castel | A61H 23/0245 601/2 |
| 2012/0016239 A1 | * | 1/2012 | Barthe | A61B 8/0858 600/439 |
| 2012/0065494 A1 | * | 3/2012 | Gertner | A61B 5/055 600/411 |
| 2013/0338545 A1 | * | 12/2013 | Azhari | A61N 7/02 601/2 |
| 2014/0309173 A1 | * | 10/2014 | Dreher | A61K 8/64 514/18.8 |
| 2016/0220804 A1 | * | 8/2016 | Khormaei | A61M 37/0092 |
| 2019/0060675 A1 | * | 2/2019 | Krone | A61N 7/00 |

* cited by examiner

*Primary Examiner* — Baisakhi Roy
(74) *Attorney, Agent, or Firm* — Riverside Law LLP

(57) ABSTRACT

The presented methods and devices may provide at least one treatment action leading to one or more treatment effects including influencing the tissue to enhance, renew or improve biosynthesis of at least one component of an extracellular matrix. In one embodiment, the methods and devices may provide treatment effects to skin fibroblasts and/or fasciacytes of the patient, influencing the skin fibroblasts and/or fasciacytes to enhance, renew or improve biosynthesis of hyaluronic acid.

22 Claims, 10 Drawing Sheets

METHODS AND DEVICES FOR TISSUE TREATMENT

This application claims priority from Provisional Application No. 62/783,431 filed on Dec. 21, 2018 which is incorporated herein by reference in its entirety.

FIELD OF THE INVENTION

The invention relates to methods and devices for tissue treatment.

BACKGROUND OF THE INVENTION

Human skin is tissue which is commonly treated in order to improve its visual appearance. Skin is composed of three basic layers: the epidermis, the dermis and the hypodermis. Skin includes hyaluronic acid contributing to tissue movement, dynamics, maintaining extracellular space, hydration by retaining water molecules and proliferation of cells. The dermis includes significantly more hyaluronic acid than the epidermis. By aging, the skin's hyaluronic acid is gradually damaged. Its disappearance leads to limited maintenance, reduced functionality of the tissue and cosmetic changes in the tissue. Factors contributing to this change include hormonal changes, redistribution of adipose tissue, the force of gravity, and environmental factors such as sun exposure and smoking.

Existing approaches to repair or replenish hyaluronic acid in the skin include the use of topically applied cosmetic lotions or creams including exogenous forms of hyaluronic acid. Another approach is application of exogenous hyaluronic acid as fillers applied by inserting a needle or cannula into the skin. However, the exogenous hyaluronic acid is cleared away from the skin and degraded by the body. Therefore, the application of exogenous hyaluronic acid may not lead to the desired improvement in appearance of the skin.

Thus, there is a need in the art for new methods and devices providing reparation and replenishment of hyaluronic acid in the skin. The present invention satisfies these needs.

SUMMARY OF THE INVENTION

Presented methods and devices may provide at least one treatment action leading to one or more treatment effects including influencing the tissue to enhance, renew or improve biosynthesis of at least one component of an extracellular matrix. In one embodiment, the methods and devices may provide treatment effects to skin fibroblasts and/or fasciacytes of the patient, influencing the skin fibroblasts and/or fasciacytes to enhance, renew or improve biosynthesis of hyaluronic acid. In one embodiment, the presented methods and devices may influence the tissue or cells to enhance, renew or improve biosynthesis of hyaluronic acid.

Methods of treatment may include the use of a combination of energies to provide treatment actions to influence cells of a patient. The combination of energies may include a combination of two or more types of energy. In one embodiment, the methods of treatment may include the use of a combination of radiofrequency energy and ultrasound energy.

The present methods and devices may provide improved soft tissue treatment, mainly in skin regions, such as improving skin laxity, skin tightening, or wrinkle reduction.

DETAILED DESCRIPTION

Figure 1A:
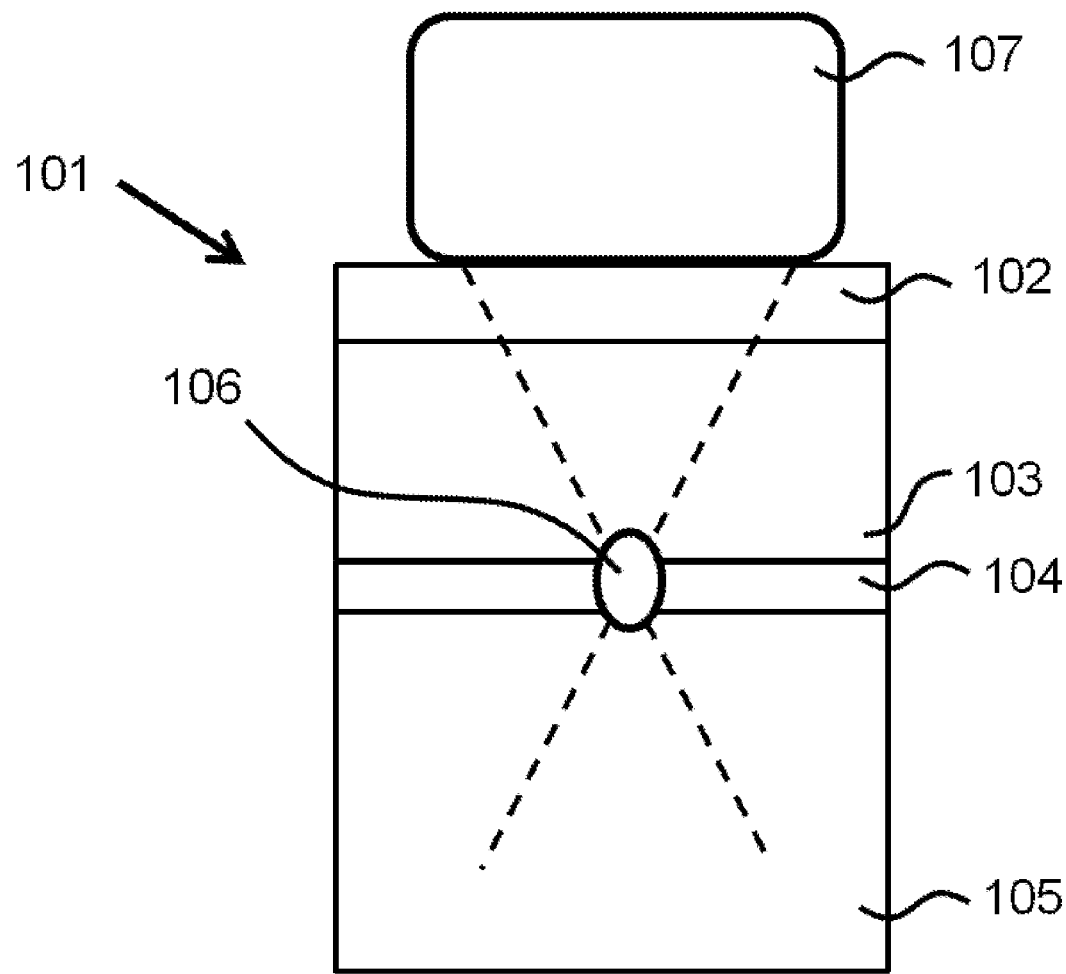
FIG. 1A is an example of mechanical stimulation of tissue.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Skin, as used herein, includes the epidermis, dermis and hypodermis. All skin layers may include connective tissue. The dermis further includes two layers: pars papillaris (papillary dermis) and pars reticularis (reticularis dermis). The layers of skin may include fibroblasts synthetizing hyaluronic acid and other components of extracellular matrix and/or connective tissue including other polysaccharides, fibronectin, laminins, glycoproteins, proteoglycans, and matricellular proteins. Hyaluronic acid can be found in the epidermis, dermis and hypodermis, but in different concentrations. The content of hyaluronic acid in the dermis may be significantly higher than that of the epidermis. In comparison to the dermal layers, the papillary dermis may include greater levels of hyaluronic acid than the reticular dermis. In the hypodermis, only traces of hyaluronic acid can be found. The hyaluronic acid may also by synthetized by fibroblasts and/or fasciacytes, fibroblast-like cells in fascia or above the muscle. The fascia is a layer of connective tissue. Fasciacytes may be located primarily in the facial fascia or between the facial muscles and fascia.

In the epidermis, hyaluronic acid may be found in high concentrations in the epidermal basal layer (sometimes referred as stratum basale or stratum germinativum), including keratinocytes.

The papillary dermis is more superficial layer of the dermis. The papillary dermis includes elastin and collagen fibers together with other components of extracellular matrix and/or connective tissue.

The reticular dermis is a lower layer of the dermis including a dense concentration of collagen, elastin and other components of extracellular matrix and/or connective tissue. The reticular dermis includes active fibroblasts synthetizing hyaluronic acid and other components of extracellular matrix and/or connective tissue. The reticular dermis plays an important role in dermal regeneration. Hyaluronic acid is synthetized by a compartment of a cell, wherein the synthesis includes a reaction provided by hyaluronan synthase. There are three distinct types of hyaluronan synthase, abbreviated HAS1, HAS2 and HAS3.

Glycosaminoglycans are long unbranched polysaccharides including repeating disaccharide units. The glycosaminoglycans may include hyaluronic acid, dermatan sulfate, keratan sulfate, chondroitin sulfate or heparan sulfate.

Hyaluronic acid, sometimes referred to as "hyaluronan" means a polymer of disaccharides, wherein the disaccharides are D-glucuronic acid and N-acetyl-D-glucosamine. Disaccharides are linked via alternating $\beta$-(1→4) and/or $\beta$-(1→3) glycosidic bonds. A polymer may be at least 10,000, 15,000, or more preferably 25,000 disaccharide repeats in length. A polymer has an average molecular weight in the range of 1000 to 100,000,000 Da or 5000 Da to 20,000,000 Da.

The presented devices and methods may be used for stimulation of the skin, epidermis, epidermal basal layer, dermis, papillary dermis and/or reticular dermis for improved and/or enhanced synthesis of at least one component of extracellular matrix and/or connective tissue including glycosaminoglycans, polysaccharides, fibronectin, laminins, glycoproteins, proteoglycans, and/or matricellular proteins. Also, the presented devices and methods may be used for stimulation of the tissue, skin, epidermis, epidermal basal layer, dermis, papillary dermis and/or reticular dermis for improved, renewed and/or enhanced biosynthesis of hyaluronic acid in a skin by application of one or more types of energy. In addition, the presented devices and methods may be used to increase a concentration of hyaluronic acid in synovial fluid in joints, tendons, cartilage, blood vessels, and/or ligaments (e.g. Cooper's ligament).

The methods of treatment may include application of one type of energy. In addition, the methods of treatment may include a combination of one type of energy and at least one other type of energy. Energy may be applied in a continuous and/or pulsed manner. One or more types of energy may be applied to tissue, skin, epidermis, epidermal basal layer, dermis, papillary dermis, reticular dermis, hypodermis, fascia, tendon, ligament, and/or synovial fluid. Both types of energy may be applied simultaneously or sequentially. In a simultaneous application, both types of energy may be applied at the same time. In a sequential application, one type of energy may be applied after another type of energy. In some embodiments, the application of one type of energy may overlap with application of another type of energy. The overlap of the application of one type of energy with the application of another type of energy may occur at discrete time intervals in the range of 0.01 to 300 seconds, more preferably in the range of 0.05 to 150 seconds, most preferably in the range of 0.1 to 80 seconds. One or more types of energy may be delivered by one or more energy delivery elements.

The application of one or more types of energy may provide treatment effects including enhanced biosynthesis, renewed biosynthesis or improvement of biosynthesis of at least one component of an extracellular matrix and/or connective tissue including glycosaminoglycans, polysaccharides, fibronectin, laminins, glycoproteins, proteoglycans, and/or matricellular proteins. In addition, the treatment effect may include proliferation of cells (including fibroblasts and/or fasciacytes). The application of one or more types of energy may provide treatment effects to tissue including enhancement, renewal or improvement of biosynthesis of at least one component of the extracellular matrix and/or connective tissue including glycosaminoglycans, polysaccharides, fibronectin, laminins, glycoproteins, proteoglycans, and/or matricellular proteins. The tissue may be skin. A treatment effect may be caused by one or more treatment actions. One or more treatment actions may lead to a treatment effect. One type of energy may provide one treatment action, while another type of energy may provide another treatment action. In still another embodiment, one type of energy and another type of energy may provide the same or similar treatment action. A first type of energy may provide a first treatment action while a second type of energy may provide a second treatment action. In another embodiment the treatment action leading to a treatment effect may be the result of a synergy of two different types of energy. Treatment actions may be caused by sufficient application of one or more types of energy.

The application of one or more types of energy may provide treatment effects to cells of the patient wherein the treatment effect may include influencing the cells to enhance, renew or improve biosynthesis, deposition and/or production of at least one component of the extracellular matrix and/or connective tissue. The application of one or more types of energy may provide treatment effects to cells of the patient, wherein the treatment effect may include influencing the cells to enhance, renew or improve biosynthesis, deposition, and/or production of at least glycosaminoglycan. The application of one or more types of energy may provide treatment effects to cells of the patient, wherein the treatment effect may include influencing the cells to enhance, renew or improve biosynthesis, deposition and/or production of hyaluronic acid. In one embodiment, the application of one or more types of energy may provide treatment actions causing a treatment effect to skin fibroblasts of the patient, wherein the treatment effect may include influencing the skin fibroblasts to enhance, renew or improve biosynthesis, deposition and/or production of hyaluronic acid. Also, the treatment effect may include an improvement of activity in at least one cell organelle (e.g. Golgi apparatus) or increased production of at least one enzyme e.g. at least one enzyme contributing to nascent hyaluronan synthesis or at least one type of hyaluronan synthase. In addition, the treatment effect may include an improvement in deposition of newly synthetized components of extracellular matrix and/or connective tissue in already present extracellular matrix and/or connective tissue.

The methods may be used for treatment of body regions including the face, head, neck, breast, arms, hands, torso, thighs, pubic area, limbs, upper part of a torso, armpit and/or buttocks. In addition, the methods may be used for treatment of facial parts including temples, cheek (either lower and/or upper cheek), mid-lower face, submentum, nose, jaw, mouth, eyebrow, forehead, periorbital area, perioral area, and/or chin.

The presented devices and methods of treatment may be used for treatment of wrinkles, sagging skin, acne, stretch marks, cellulite, collagen deficiency, elastin deficiency, hyaluronic acid deficiency, dermatitis and/or scars.

Application of one or more energies according to this invention may provide one or more treatment actions. A treatment effect may be caused by and/or a result of one action or a combination of at least two treatment actions. The treatment action may be a non-targeted treatment action or a targeted treatment action. A treatment may include application of one type of energy or combined application of at least two types of energies. Each type of energy may provide a different or the same treatment action. In one embodiment one type of energy may provide a non-targeted treatment action while another type of energy may provide a targeted treatment action. In another embodiment, one type of energy may provide a non-targeted treatment action, while another type of energy may provide a non-targeted treatment action. In still another embodiment one type of energy may provide a targeted treatment action while another type of energy may provide targeted treatment action. In another embodiment, the treatment action may be a result of a synergy of at least two types of energy. One type of energy providing a non-targeted treatment action may be electromagnetic energy. A treatment action, targeted treatment action and/or a non-targeted treatment action may include heating, vibrational movement of at least one cell, vibrational movement of an extracellular matrix, apoptosis, necrosis, cavitation, temperature decrease, hypothermic shock and/or hyperthermic shock. Hyperthermic shock may be heat shock. Targeted heating may lead to at least partial destruction of an extracellular matrix and/or cells. In one embodiment, a non-targeted treatment action may include heating, while a targeted treatment action provided by another type of energy may include vibrational movement of at least one cell, vibrational movement of an extracellular matrix, apoptosis, targeted heating and/or targeted cooling. A treatment action may be provided by one or more energies in a degree sufficient to cause a treatment effect. Sufficient application of one or more types of energy may refer to application in a degree sufficient to a cause treatment action (e.g. sufficient application of electromagnetic energy may lead to heating).

At least one treatment action may be applied to the tissue, skin, epidermis, epidermal basal layer, dermis, papillary dermis, reticular dermis, hypodermis, tendons, cartilage, blood vessels, ligaments, and/or fascia. When the treatment action provided by of one or more energies include heating, the temperature of the tissue may be increased to a value in a range of 30° C. to 110° C. or 32° C. to 80° C. or 33° C. to 65° C. or 35° C. to 65° C. or 37° C. to 55° C. or 37° C. to 48° C. The temperature of the skin surface may be increased to a value in the range of 32° C. to 90° C. or 35° C. to 65° C. or 37° C. to 55° C. The temperature of the epidermis may be increased to a value in the range of 32° C. to 90° C. or 35° C. to 65° C. or 37° C. to 55° C. The temperature of the epidermal basal layer may be increased to a value in the range of 32° C. to 90° C. or 35° C. to 65° C. or 37° C. to 55° C. The temperature of the dermal layer may be increased to a value in the range of 32° C. to 90° C. or 35° C. to 65° C. or 37° C. to 55° C. The temperature of the papillary dermal layer may be increased to a value in the range of 32° C. to 90° C. or 35° C. to 65° C. or 37° C. to 55° C. The temperature of the reticular dermal layer may be increased to a value in the range of 32° C. to 90° C. or 35° C. to 65° C. or 37° C. to 55° C. The temperature of the hypodermis may be increased to a value in the range of 32° C. to 90° C. or 35° C. to 65° C. or 37° C. to 55° C.

A non-targeted treatment action provided to a tissue by an energy source may provide enhanced delivery of nutrients to the fibroblasts and other cells reacting to or recovering from the targeted treatment action. Also, a non-targeted treatment action may contribute more to homogenous distribution of targeted treatment actions in the tissue.

Without being bound to any theory or mechanism of action, the treatment effect provided by one or more types of energy providing at least one treatment action may include induced proliferation of cells (including fibroblasts and/or fasciacytes), and/or improvement of functional ability or stability of cells. When a treatment includes energy providing a treatment action, the treatment action may cause a treatment effect in the epidermis, epidermal basal layer, dermis, reticular dermis and/or papillary dermis. The cells (including fibroblasts) may be induced sufficiently by at least one treatment action to start or increase production of components of the extracellular matrix and/or connective tissue, for example hyaluronic acid. The treatment action provided by one or more types of energy may lead to a treatment effect. A treatment effect may include a biological response to at least one treatment action, e.g. to heating, vibrational movement of at least one cell, vibrational movement of an extracellular matrix and/or to targeted heating (including heat shock) leading to partial destruction of at least one component of extracellular matrix e.g., glycosaminoglycan (e.g. hyaluronic acid), elastin or collagen. The heating of the reticular dermis and/or epidermal basal layer may be sufficient or be applied to a degree sufficient to induce proliferation of cells (e.g. fibroblasts) or to induce a biological response. A biological response may include increased production and/or increased activity of heat shock proteins and/or chaperones (e.g. Hsp10, Hsp27, Hsp47, Hsp70, Hsc70, Hsp72 or Hsp90) leading to increased proteosynthesis and/or increased ability to decompose nutrients needed for biosynthesis of one or more components of extracellular matrix and/or resistance of cells, cell organelles, enzymes or extracellular matrix to radical oxygen species. The biological response may include modulation of organelle function which may be represented e.g. by increased production or synthesis of a precursor of at least one glycosaminoglycan (e.g. hyaluronic acid) in a Golgi apparatus. Additionally, a biological response may include upregulation, increased activity and/or increased proteosynthesis of at least one type of hyaluronan synthase (e.g. HAS1, HAS2 and/or HAS3) leading to improved, enhanced, or renewed synthesis of hyaluronic acid and its deposition into the extracellular matrix in the region of the epidermis, dermis, hypodermis, mainly in reticular dermis, papillary dermis and/or epidermal basal layer. Sufficiently induced fibroblasts may produce components of the extracellular matrix, e.g. collagen, elastin and/or at least one type of glycosaminoglycan (e.g. hyaluronic acid).

A treatment effect may include e.g. enhancement of biosynthesis of glycosaminoglycans, which may occur during treatment and/or after treatment. In one embodiment, the treatment effect includes e.g. enhancement of biosynthesis of glycosaminoglycans, (e.g. hyaluronic acid), and may occur after treatment.

The energy may be applied to a dermis, papillary dermis, reticular dermis, hypodermis, epidermis and/or basal layer of the dermis. When the energy is applied to the dermis, it may be applied to penetration depth in a range of 0.1 mm to 10 mm or 0.2 mm to 5 mm. FIG. 1A shows an exemplary embodiment of a treatment of skin 101 including epidermis 102, papillary dermis 103, reticular dermis 104 and hypodermis 105. Papillary dermis 103 and reticular dermis 104 are parts of the dermis. Energy providing a treatment action may emerge from an applicator 107. As shown in the exemplary embodiment shown in FIG. 1A, the energy may provide a targeted treatment action and create a target area 106 in the reticular dermis 104 and partly inside papillary dermis 103 and/or hypodermis 105. In some embodiments, the target area 106 with its boundaries may be located only in the papillary dermis 103, reticular dermis 104 or hypodermis 105.

Figure 1B:
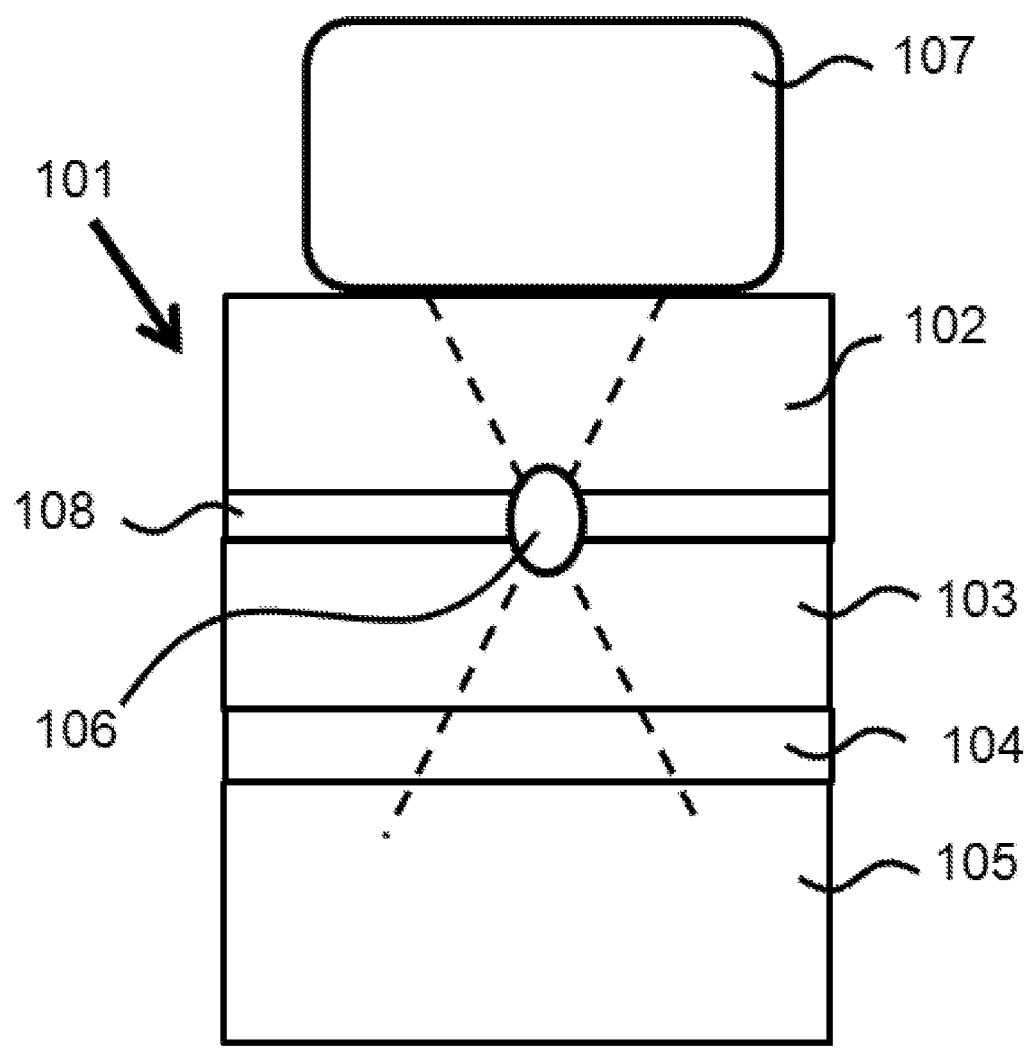
FIG. 1B is another example of mechanical stimulation of tissue

When the energy is applied to basal layer of epidermis, it may be applied to a penetration depth in a range of 0.2 mm to 5 mm or 0.2 mm to 3 mm. FIG. 1B shows another exemplary embodiment of treatment of skin 101 including epidermis 102, epidermal basal layer 108, papillary dermis 103, reticular dermis 104 and hypodermis 105. Energy providing a targeted treatment action may emerge from an applicator 107 and create a target area 106 in the epidermal basal layer 108 and partly in the epidermis 102, papillary dermis 103, and/or reticular dermis 104. In some embodiments, the target area 106 with its boundaries may be located only in the epidermis 102, epidermal basal layer 108 or papillary basal layer 103.

A target area may have a volume in the range of 0.001 $mm^3$ to 1500 $mm^3$ or 0.1 $mm^3$ to 1400 $mm^3$ or 4 $mm^3$ to 1000 $mm^3$ or 8 $mm^3$ to 1000 $mm^3$ or 10 $mm^3$ to 1000 $mm^3$. In one embodiment, the target area may not penetrate or pierce the surface of the tissue or skin. The target area therefore does not comprise the surface of the skin.

The types of energy may include electromagnetic energy, mechanical stimulation, thermal energy, electric energy, magnetic energy and/or plasma. One or more types of energy may be applied to tissue, skin, epidermis, epidermal basal layer, dermis, papillary dermis, reticular dermis, hypodermis and/or fascia. In one embodiment, one or more types of energy may be applied to the epidermis, epidermal basal layer, dermis, papillary dermis and/or reticular dermis.

Electromagnetic energy may be light, radiofrequency energy or microwave energy. The application of electromagnetic energy may lead e.g. to heating of the tissue.

The frequency of radiofrequency energy may be in the range of 10 kHz to 300 GHz or 300 kHz to 10 GHz or 400 kHz to 6 GHz. In one narrower embodiment, the frequency of radiofrequency energy may be in the range of 100 kHz to 550 MHz or 250 kHz to 500 MHz or 350 kHz to 100 MHz or 500 kHz to 80 MHz. In an even more specific embodiment, the frequency of the radiofrequency energy may be in the range of 250 kHz to 50 MHz or 350 kHz to 10 MHz. Output power of the radiofrequency energy may be less than or equal to 450, 300, 250 or 220 W. The radiofrequency energy may be applied in or close to the ISM bands of 6.78 MHz, 13.56 MHz, 27.12 MHz, 40.68 MHz, 433.92 MHz, 915 MHz, 2.45 GHz and 5.8 GHz. Radiofrequency energy may provide energy flux on the surface of the applicator and/or on the surface of the treated tissue (e.g. skin) in the range of 0.001 $W·cm^{-2}$ to 1500 $W·cm^{-2}$ or 0.01 $W·cm^{-2}$ to 1000 $W·cm^{-2}$ or 0.5 $W·cm^{-2}$ to 500 $W·cm^{-2}$. The radiofrequency energy may be applied in a monopolar, bipolar, unipolar and/or multipolar manner. Monopolar application of radiofrequency energy may include use of a neutral electrode in cooperation with an active RF electrode.

Electromagnetic energy may include light. Light may be coherent, depolarized, polarized, monochromatic or polychromatic. Light may be applied in pulses with a duration in the range of 0.1 μs to 10000 ms or 1 μs to 5000 ms or 2 μs to 2500 ms or 5 μs to 1000 ms. The wavelength of the light may be in the range of 200 nm to 15000 nm, more preferably in the range of 250 nm to 10000 nm, even more preferably in the range of 300 nm to 5000 nm, most preferably in the range of 400 nm to 3000 nm. Applied light may provide energy flux in the range of 0.005 $W/cm^2$ to 75 $W/cm^2$, more preferably in the range of 0.01 $W/cm^2$ to 60 $W/cm^2$ and most preferably in the range of 0.01 $W/cm^2$ to 50 $W/cm^2$. Methods of treatment may include use of a spot size defined as the surface of tissue treated by the light. One beam may provide an energy spot having an energy spot size defined as a surface of tissue irradiated by one beam of light. One light source may provide one or more energy spots e.g. by splitting one beam into a plurality of beams. The energy spot size may be in the range of 0.001 $cm^2$ to 600 $cm^2$, more preferably in the range of 0.005 $cm^2$ to 300 $cm^2$, most preferably in the range of 0.01 $cm^2$ to 100 $cm^2$. Energy spots of different and/or the same wavelength may be overlaid or may be separated. Two or more beams of light may be applied to the same spot at the same time or with a time gap ranging from 0.1 μs to 30 seconds. Energy spots may be separated by at least 1% of their diameter, and in some embodiments energy spots closely follow each other and/or are separated by a gap ranging from 0.1 cm to 20 cm.

Energy may be also applied in a narrower spectral band. The wavelength of the light may be about 254 nm, 405 nm, 450 nm, 532 nm, 560 nm, 575 nm, 635 nm, 660 nm, 685 nm, 808 nm, 830 nm, 880 nm, 915 nm, 970 nm, 980 nm, 1060 nm, 1064 nm, 1320 nm, 1440 nm and/or 1470 nm, 1540 nm, 1550 nm, 1565 nm, 2940 nm, or 11600 nm. In some embodiments, the wavelength may be changed during treatment. Methods of treatment may include application of an aiming beam of any visible (e.g. red, blue, green or violet) color.

Methods of treatment may include application of a low level light. The output power of the source of low level light may be in the range of 0.1 mW to 600 mW, more preferably in the range of 1 mW to 500 mW, even more preferably in the range of 1.5 mW to 475 mW, most preferably in the range of 3 mW to 450 mW. Energy flux provided by low level light may be in the range of 0.01 $W/cm^2$ to 30 $W/cm^2$, more preferably in the range of 0.05 W/cm² to 25 W/cm² and most preferably in the range of 0.1 W/cm² to 20 W/cm².

Methods of treatment may include application of a high level light. In this case, the output power of the source of high level light may be in the range of 0.1 W to 30 W, more preferably in the range of 0.2 W to 25 W, most preferably in the range of 0.35 W to 15 W. Energy flux provided by high level light may be in the range of 0.01 W/cm² to 75 W/cm², more preferably in the range of 0.05 W/cm² to 60 W/cm² and most preferably in the range of 0.1 W/cm² to 50 W/cm².

Methods of treatment may include application of mechanical stimulation. Mechanical stimulation may be ultrasound energy, shock wave, acoustic wave energy or targeted mechanical stimulation.

Ultrasound energy may have a frequency in the range of 20 kHz to 25 GHz or 20 kHz to 1 GHz or 50 kHz to 250 MHz to 100 kHz to 100 MHz. In one embodiment, the frequency of the ultrasound energy may be in the range of 20 kHz to 80 MHz or 50 kHz to 50 MHz or 150 kHz to 20 MHz. The output power of the ultrasound energy on the surface of the applicator may be less than or equal to 20 W or 15 W or 10 W or 5 W. Ultrasound energy may provide energy flux on the surface of the applicator and/or on the surface of the treated tissue (e.g. skin) in the range of 0.001 W/cm² to 250 W/cm², more preferably in the range of 0.005 W/cm² to 50 W/cm², even more preferably in the range of 0.01 W/cm² to 25 W/cm², most preferably in the range of 0.05 W/cm² to 20 W/cm². Ultrasound energy may be focused or defocused. Treatment depth of ultrasound energy may be in the range of 0.1 mm to 100 mm or 0.2 mm to 50 mm or 0.25 mm to 25 mm or 0.3 mm to 15 mm. At a depth of 5 mm the ultrasound energy may provide an energy flux in the range of 0.01 W/cm² to 20 W/cm² or 0.05 W/cm² to 15 W/cm². The ratio between the output power of ultrasound energy on the surface of the applicator and the output power of the ultrasound energy on the surface of the acoustic window (W/cm²) may be in the range of 0.001 to 1500, more preferably in the range of 0.002 to 500, even more preferably in the range of 0.005 to 250 even more preferably 0.01 to 100, most preferably in the range of 0.2 to 50. An ultrasound beam may have a beam non-uniformity ratio ($R_{BN}$) in the range of 0.1 to 20 or 2 to 15 to 4 to 10. In addition, an ultrasound beam may have a beam non-uniformity ratio below 15 or 10. An ultrasound beam may be divergent, convergent and/or collimated. The temperature of tissue, skin and/or skin surface may be increased by application of ultrasound energy to a value in the range of 32° C. to 90° C. or 35° C. to 65° C. or 37° C. to 55° C.

The ultrasound energy may be a targeted ultrasound energy which is able to provide effects similar to focused ultrasound energy into a bigger area. Targeted ultrasound energy is not limited to a small focus point, as focused ultrasound energy is. Targeted ultrasound energy may have a different effective radiating area, defined as beam cross-sectional area determined at a distance of 3 mm from the from the surface of the applicator and multiplied by a dimensionless factor equal to 1.354. The effective radiating area of targeted ultrasound energy may be in the range of 0.1 cm² to 1.5 cm², more preferably in the range of 0.25 cm² to 1 cm². The ultrasound beam of targeted ultrasound may have a beam non-uniformity ratio below 8. The treatment depth of targeted ultrasound energy may be in the range of 0.1 mm to 80 mm or 0.2 mm to 75 mm or 0.25 mm to 50 mm or 0.25 mm to 25 mm. Targeted ultrasound energy may provide energy flux on the surface of the applicator and/or on the surface of the treated tissue (e.g. skin) in the range of 0.001 W/cm² to 200 W/cm², more preferably in the range of 0.005 W/cm² to 50 W/cm², even more preferably in the range of 0.01 W/cm² to 25 W/cm², most preferably in the range of 0.1 W/cm² to 20 W/cm². The frequency of targeted ultrasound energy may be in a range of 100 kHz to 20 MHz or 200 kHz to 10 MHz or 250 kHz to 8 MHz. Energy flux of the targeted ultrasound energy measured in water at 5 mm deep below the contact surface of the applicator may be in the range of 0.1 W/cm² to 15 W/cm² or 0.25 W/cm² to 10 W/cm² or 0.5 W/cm² to 6 W/cm². The temperature of the tissue 3 mm below the surface of the applicator providing targeted ultrasound energy may be increased to a value in the range of 39° C. to 55° C. or 40° C. to 50° C. Targeted ultrasound energy may be applied and provide treatment action to the epidermis, epidermal basal layer, dermis (including papillary dermis, reticular dermis) and/or hypodermis. The temperature of tissue, skin and/or skin surface may be increased by application of targeted ultrasound energy to a value in the range of 32° C. to 90° C. or 35° C. to 65° C. or 37° C. to 55° C.

The ultrasound energy may be transferred to the tissue through an acoustic window. In one embodiment, the RF electrode may act as the acoustic window. The acoustic window may have surface area in the range of 0.01 cm² to 250 cm² or 0.1 cm² to 150 cm² or 0.2 cm² to 100 cm² or 0.2 cm² to 80 cm². The output power of targeted ultrasound energy on the surface of the applicator may be up to 2.5 W or 4 W or 10 W. The relatively low output power may provide ultrasound energy also outside of a distinct target area. Therefore, at least 5% of the output power of ultrasound energy may be transferred outside of the distinct target area. The ratio between the output power of targeted ultrasound energy on the surface of the applicator and the surface of the acoustic window (W/cm²) may include a range of intervals contributing to a treatment effect. The ratio between the output power of targeted ultrasound energy on the surface of the applicator and the surface of the acoustic window (W/cm²) may be in the range of 0.001 to 1500, more preferably in the range of 0.01 to 500, even more preferably in the range of 0.01 to 100, most preferably in the range of 0.2 to 50.

Shock wave, acoustic wave or targeted mechanical stimulation may be generated by electrohydraulic, electromagnetic, piezoelectric, pneumatic (e.g. ballistic) principles. Shock wave, acoustic wave or targeted mechanical stimulation may be non-focused/radial, planar or moderately focused. Shock wave, acoustic wave or targeted mechanical stimulation may provide energy flux density in the range of 0.001 mW/mm² to 160 mW/mm² or 0.001 mW/mm² to 100 mWmm² or 0.001 mW/mm² to 50 mW/mm². In an example of ballistic generation, for example with a bullet hitting a bumper, the repetition rate of bullet strikes may be in the range from 0.1 Hz to 250 Hz or 0.5 to 100 Hz to 1 Hz to 80 Hz.

Other possible types of energy or energies to be applied for the same or similar treatment effect and additional parameters may be found in U.S. Pat. No. 10,039,929 and co-pending U.S. patent application Ser. No. 16/052,369, both of which are incorporated herein by reference in their entireties.

A combination of two or more types of energy may include a combination of energy providing a thermal effect with at least one another type of energy. Energy providing a thermal effect may provide a treatment action including heating and/or heat shock. Energy providing a thermal effect may include thermal energy and may be applied from an applicator e.g. including a bolus filed with fluid. The energy providing a thermal effect may include electromagnetic energy. Another type of energy may be light energy, mechanical stimulation (including ultrasound), electric energy, cooling, magnetic energy and/or plasma. Combined application of types of energy may provide heating of tissue. Tissue may be skin including epidermis, basal layer of the epidermis, papillary dermis, reticular dermis and/or hypodermis. The temperature of the tissue may be increased to a value in a range of 30° C. to 110° C. or 32° C. to 80° C. or 33° C. to 65° C. or 35° C. to 65° C. or 37° C. to 55° C. or 37° C. to 48° C. The temperature of the skin surface may be increased to a value in the range of 32° C. to 90° C. or 35° C. to 65° C. or 37° C. to 55° C. The temperature of the epidermis may be increased to a value in the range of 32° C. to 90° C. or 35° C. to 65° C. or 37° C. to 55° C. The temperature of the epidermal basal layer may be increased to a value in the range of 32° C. to 90° C. or 35° C. to 65° C. or 37° C. to 55° C. The temperature of the dermal layer may be increased to a value in the range of 32° C. to 90° C. or 35° C. to 65° C. or 37° C. to 55° C. The temperature of the papillary dermal layer may be increased to a value in the range of 32° C. to 90° C. or 35° C. to 65° C. or 37° C. to 55° C. The temperature of the reticular dermal layer may be increased to a value in the range of 32° C. to 90° C. or 35° C. to 65° C. or 37° C. to 55° C. The temperature of the hypodermis layer may be increased to a value in the range of 32° C. to 90° C. or 35° C. to 65° C. or 37° C. to 55° C. One or more energies providing thermal effect may also provide at least one targeted or non-targeted treatment effect, e.g. vibrational movement of at least one cell, vibrational movement of extracellular matrix and/or apoptosis.

In one embodiment, a thermal effect may be cooling. Cooling may be provided by cooling means. The cooling may ensure that the temperature on the surface of the skin and/or the applicator does not exceed 55, 50, 48, 46 or 44° C. In another embodiment, cooling may induce a reverse thermal gradient in tissue. By providing a reverse thermal gradient during treatment, one layer of the skin may have a different temperature than another layer of the skin. When the dermis, reticular dermis and/or papillary dermis has a temperature in the range of 39° C. to 46° C., the epidermis and/or surface of the tissue may have a temperature in the range of 32° C. to 38° C.

Cooling may be provided during, before, and/or after the treatment with the combined application of energy providing a thermal effect and another type of energy. Cooling before treatment may also provide an environment for sudden heat shock, while cooling after therapy may provide faster regeneration after heat shock. A device may provide cooling by cooling means, e.g. a coolant reservoir, active cooling element and/or cooled element. The coolant reservoir may include coolant, which may be applied (e.g. sprayed) onto and/or into tissue and/or used to cool the cooling element. Coolant may include saline, water, alcohol, a water/alcohol mixture, cold air, carbon dioxide and/or liquid nitrogen. The temperature of the coolant may be in the range of −200° C. to 37° C. The cooled element may include thermally conductive materials e.g. glass, sintered ceramic, gel, ice slurry and/or metal. An active solid cooling element may include a thermoelectric element. An active solid cooling element may comprise an active side cooling the tissue and a passive side which may be cooled by a liquid (e.g. water), a gas coolant (e.g. air), a coolant and/or a Peltier element. Cooling means may cool the at least one energy delivery element, which may cool the skin. The temperature of the cooling element during the treatment may be in the range of −80° C. to 37° C. or −70° C. to 37° C. or −60° C. to 35° C.

In one embodiment a combination of types of energy may include a combination of targeted and non-targeted energy. In another embodiment, one type of energy may provide a treatment action represented by heating (e.g. non-targeted) while another type of energy may provide another treatment action represented by targeted heating. In still another embodiment, one type of energy may provide a treatment action represented by vibrational movement of at least one cell while another type of energy may provide another treatment action represented by heating. In still another embodiment, one type of energy may provide a treatment action represented by vibrational movement of extracellular matrix while another type of energy may provide another treatment action represented by heating. In still another embodiment, one type of energy may provide a treatment action represented by non-targeted heating of extracellular matrix while another type of energy may provide another treatment action represented by heating of fibroblasts. In still another embodiment, one type of energy may provide a treatment action represented by non-targeted heating of synovial fluid or ligament while another type of energy may provide another treatment action represented by targeted heating of synovial fluid or ligament.

When the targeted energy is applied and the targeted energy provides a targeted treatment action represented by targeted heating, the temperature in the target area may be up to 2° C. or 5° C. or 15° C. higher than in the rest of the tissue e.g. tissue affected by another type of energy, for example a non-targeted type of energy. When the targeted treatment action is represented by targeted cooling, the temperature in the target area may be up to 15° C. or 25° C. or 45° C. lower than in the rest of the tissue e.g. the tissue outside of the target area affected by another type of energy, preferably a non-targeted type of energy. The temperature of the target area may be increased or decreased during the whole treatment.

During treatment, the skin and/or at least one of skin layer may be heated for up to 30 s, 5 minutes, 30 minutes, 60 minutes, or 5 hours. The application of energy providing a thermal effect may overlap with the application of another type of energy. The overlap of the energy providing the thermal effect with the application of another type of energy may occur at discrete time intervals in the range of 0.01 to 300 seconds, more preferably in the range of 0.05 to 150 seconds, most preferably in the range of 0.1 to 80 seconds. In another embodiment, a combination of types of energy may include a combination of targeted or non-targeted types of energy. In such a case, one or more treatment effects may be created by a synergy of combined types of energy. Synergic treatment effects may include heating of tissue e.g. skin. An advantage of synergic effects of two different types of treatment may be represented by lowered heating provided by an energy delivery element of each type of energy.

A combination of types of energy may include a combination of radiofrequency energy with a second different type of energy, e.g. light energy, mechanical energy, electric energy, magnetic energy and/or plasma. The combined energy flux of radiofrequency energy and a second type of energy on the surface of the tissue and/or on the surface of the applicator may be in the range of 0.002 W/cm$^2$ to 2500 W/cm$^2$ or 0.005 W/cm$^2$ to 2000 W/cm$^2$ or 0.01 W/cm$^2$ to 1500 W/cm$^2$. In one embodiment, an application of radiofrequency energy may be combined with an application of targeted ultrasound energy.

In one embodiment, the methods of treatment may include a combined treatment of the tissue by radiofrequency energy and ultrasound energy (e.g. targeted ultrasound energy). Both types of energy may be applied simultaneously or sequentially. Application of radiofrequency energy together with ultrasound energy may provide a treatment effect including heating on the surface of tissue by a temperature increase. The temperature of the tissue may be increased to a value in a range of 30° C. to 110° C. or 32° C. to 80° C. or 33° C. to 65° C. or 35° C. to 65° C. or 37° C. to 55° C. or 37° C. to 48° C. The temperature of the skin surface may be increased to a value in the range of 32° C. to 90° C. or 35° C. to 65° C. or 37° C. to 55° C. The temperature of the epidermis may be increased to a value in the range of 32° C. to 90° C. or 35° C. to 65° C. or 37° C. to 55° C. The temperature of the epidermal basal layer may be increased to a value in the range of 32° C. to 90° C. or 35° C. to 65° C. or 37° C. to 55° C. The temperature of the dermal layer may be increased to a value in the range of 32° C. to 90° C. or 35° C. to 65° C. or 37° C. to 55° C. The temperature of the papillary dermal layer may be increased to a value in the range of 32° C. to 90° C. or 35° C. to 65° C. or 37° C. to 55° C. The temperature of the reticular dermal layer may be increased to a value in the range of 32° C. to 90° C. or 35° C. to 65° C. or 37° C. to 55° C. The temperature of the hypodermis may be increased to a value in the range of 32° C. to 90° C. or 35° C. to 65° C. or 37° C. to 55° C. The combined energy flux of radiofrequency energy and ultrasound energy on the surface of the tissue and/or on the surface of the applicator may be in the range of 0.002 W/cm² to 1750 W/cm² or 0.005 W/cm² to 1500 W/cm² or 0.01 W/cm² to 1250 W/cm² or 0.01 W/cm² to 750 W/cm² or 0.05 W/cm² to 550 W/cm². The ratio of the frequency of radiofrequency energy to the frequency of the ultrasound energy (MHz/MHz) may be in the range of 0.0001 to 5000, more preferably in the range of 0.0005 to 500, even more preferably 0.001 to 250, most preferably in the range of 0.001 to 150. The ratio of the frequency of radiofrequency energy to the frequency of the targeted ultrasound energy (MHz/MHz) may be in the range of 0.001 to 50, more preferably in the range of 0.005 to 25, even more preferably 0.01 to 10, most preferably in the range of 0.05 to 5.

In another embodiment, the methods of treatment may include a combined treatment of the tissue by radiofrequency energy and light energy. The combined energy flux of radiofrequency energy and light on the surface of the tissue and/or on the surface of the applicator may be in the range of 0.006 W/cm² to 1550 W/cm² or 0.01 W/cm² to 1000 W/cm² or 0.015 W/cm² to 750 W/cm².

In still another embodiment, the methods of treatment may include a combined treatment of the tissue by radiofrequency energy and shock wave. The ratio of frequency of radiofrequency energy and shock wave frequency (MHz to Hz) may be in the range of 0.0005 or 200 or 0.001 to 60 or 0.005 to 30.

Methods of treatment may include a combination of radiofrequency energy and targeted ultrasound energy with a third type of energy. The third type of energy may be magnetic energy, cooling means, plasma and/or electric energy. The third type of energy may be delivered by the same device, same applicator, different applicator or different device. The third energy may be applied before, during and/or after the combined treatment with radiofrequency energy and targeted ultrasound energy.

Methods of treatment may include a combination of radiofrequency energy and targeted ultrasound energy with magnetic energy. A device and method for generation of magnetic energy is described in co-pending U.S. patent application Ser. No. 16/218,735 and U.S. provisional patent application 62/786,731, both of which are incorporated herein by reference in their entireties. Magnetic energy, providing mostly myorelaxation and/or muscle contraction, may provide further improvements to local circulation in and/or near treated tissue. Additional improvements to local circulation may lead to more homogenous heat distribution and faster delivery of nutrients to cells (e.g. fibroblasts) recovering from at least one treatment action and therefore faster regeneration of tissue.

Methods of treatment may include a combination of radiofrequency energy and targeted ultrasound energy with electric energy. Electric energy may also provide myorelaxation and/or muscle contraction for improvement of local circulation. Electric energy may be applied in pulses with a different repetition rate. Generally, the repetition rate of pulses may be in the range of 0.001 Hz to 1000 Hz or 0.05 Hz to 800 Hz or 0.1 to 600 Hz. However, the repetition rate of pulses may induce various desired effects. For example, the repetition rate of pulses inducing muscle stimulation may be in the range of 0.01 Hz up to 100 Hz or 0.05 Hz to 85 Hz or 0.1 Hz to 75 Hz. In another example, the repetition rate of pulses inducing pain relief may be in the range of 100 Hz up to 400 Hz or 105 Hz to 250 Hz or 115 Hz to 150 Hz. In still another example, the repetition rate of pulses inducing a myorelaxation may be in the range of 100 Hz up to 600 Hz or 130 Hz to 400 Hz or 150 Hz to 250 Hz. The amplitude of applied current may vary according to the patient's needs and/or the desired effect. Output voltage may be in the range of 0.001 V to 800 V and output current may be in the range of 0.001 mA to 400 mA. Electrical energy may be applied in a constant current mode, wherein the current may be in the range of 0.01 mA to 400 mA or 0.01 mA to 300 mA, or 0.01 mA to 180 mA. Output voltage may be in the range of 0.001 V to 350 V or 0.001 V to 300 V or 0.001 V to 250 V. In another embodiment, electrical energy may be applied in a constant voltage mode, wherein the output current may be in the range of 0.01 mA to 400 mA or 0.01 mA to 300 mA or 0.01 mA to 180 mA. Output voltage may be in the range of 0.001 V to 350 V or 0.001 V to 300 V or 0.001 V to 250 V. In still another embodiment, the electric energy may provide high voltage therapy.

Methods of treatment may include a combination of radiofrequency energy and targeted ultrasound energy with plasma. Plasma may provide a reduction in and/or elimination of pain, stimulation of a regenerative process, bactericidal effect and/or decreasing risk of inflammation. The temperature of provided plasma may be in the range of 18° C. to 65° C. or 25° C. to 62° C. or 30° C. to 60° C. or 32° C. to 40° C. Plasma may be applied in a range between 1 s to 60 min or 10 s to 40 min or 30 s to 30 min. Plasma may also be applied in pulses that may last between 0.1 s to 30 s, 20 s, and/or 10 s. Plasma may be produced by a voltage between electrodes in range of 100 V to 30 kV or 1 kV to 30 kV or 1 kV to 20 kV. A plasma generation module may use an electrode frequency in the range of 20 kHz to 27 MHz or 0.8 MHz to 15 MHz or 1 MHz to 14 MHz.

Figure 2A:
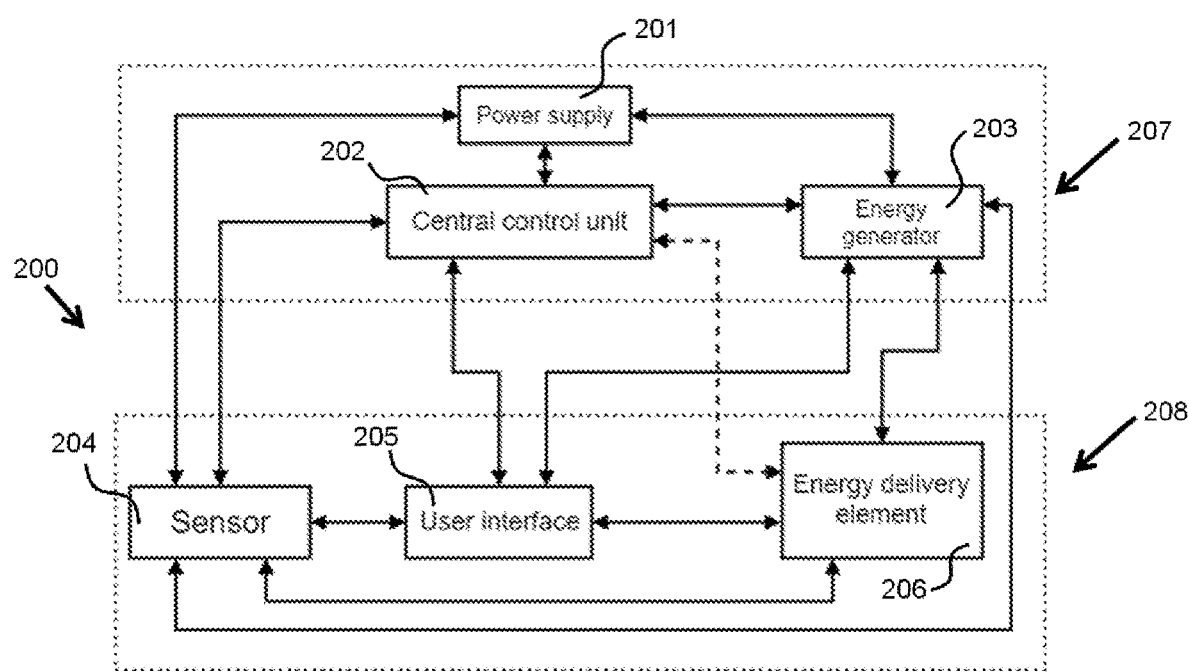
FIG. 2A is an exemplary schematic diagram of a device for treatment of tissue.
Figure 2B:
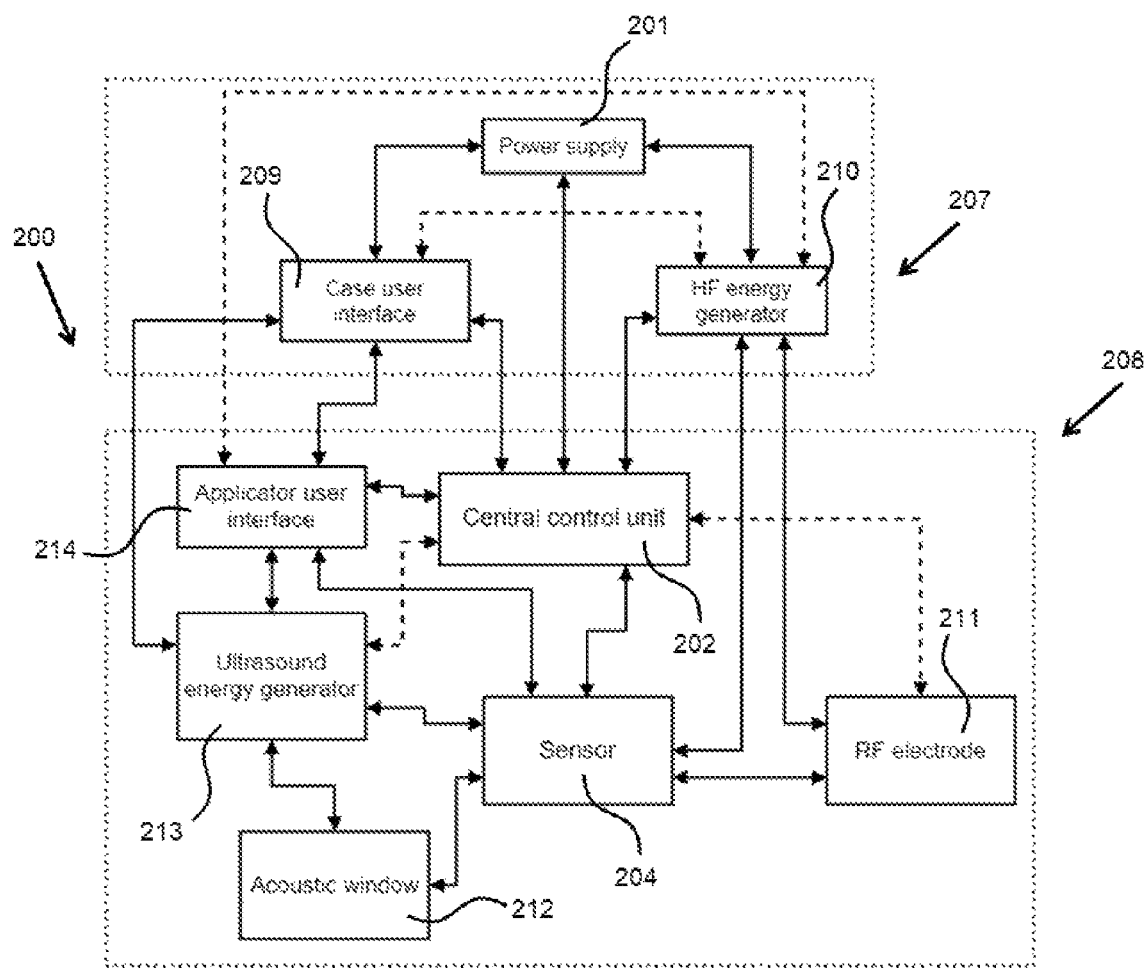
FIG. 2B is another exemplary schematic diagram of a device for treatment of tissue.
Figure 2C:
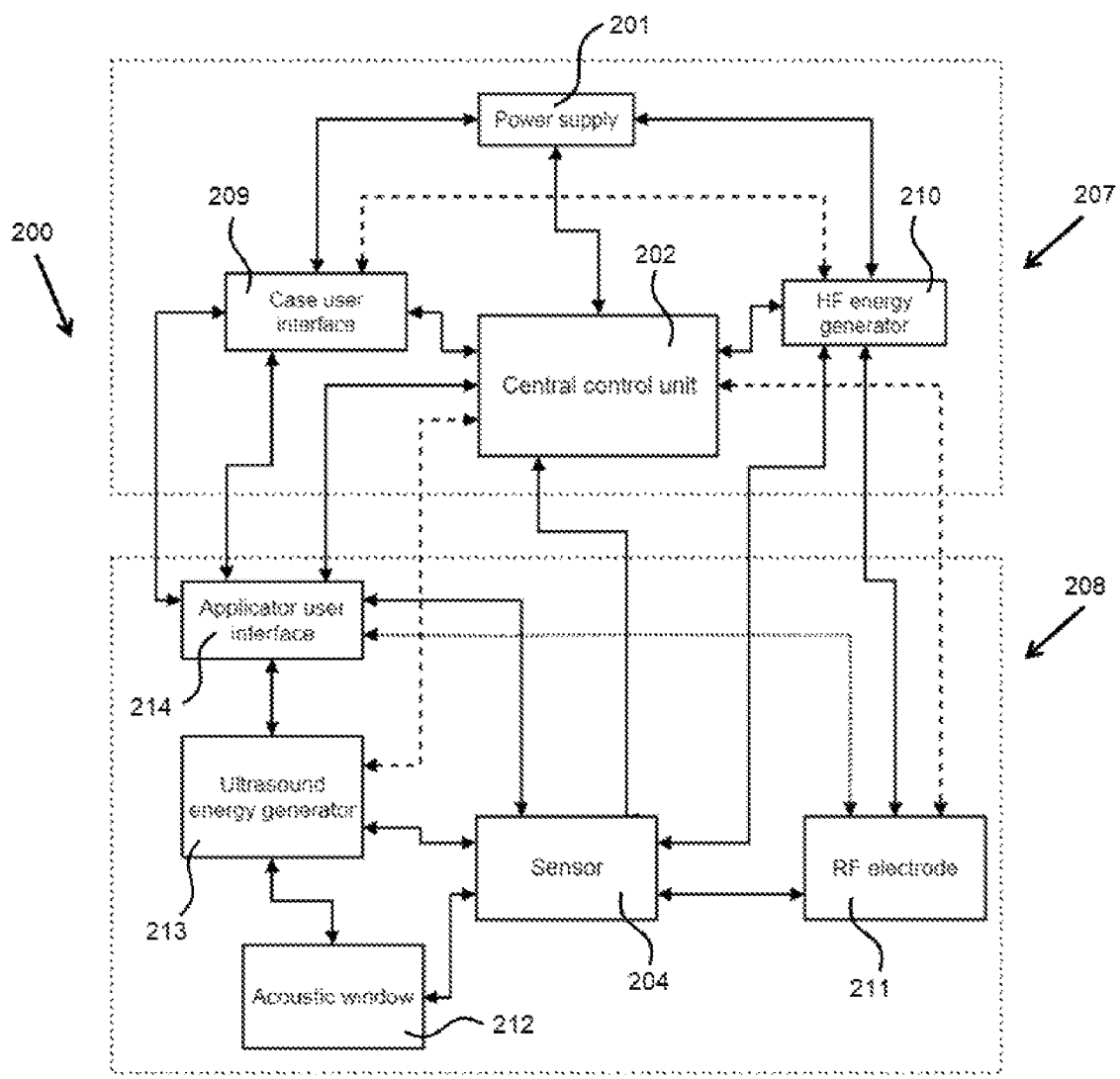
FIG. 2C is another exemplary schematic diagram of a device for treatment of tissue

Referring now to FIG. 2A, in one exemplary embodiment, device 200 may include at least one power supply 201, central control unit 202, energy generator 203, sensor 204, user interface 205, and at least one energy delivery element 206 providing at least one type of energy. Power supply 201, central control unit 202 and energy generator 203 may be part of case 207, while sensor 204, user interface 205, and at least one energy delivery element 206 may be part of applicator 208. Central control unit 202 may be connected to power supply 201, energy generator 203, user interface 205, sensor 204, and at least one energy delivery element 206

(dashed arrow). Energy generator 203 may be connected to power supply 201, sensor 204, user interface 205 and at least one energy delivery element 206. Sensor 204 may be connected to power supply 201, user interface 205 and at least one energy delivery element 206. Power supply 201, energy generator 203 and central control unit 202 may be parts of the case unit, while the sensor 206, energy delivery element 206, and user interface 205 may be parts of applicator 208.

Power supply 201 may be a disposable battery, rechargeable battery, power plug or standard power cord. Central control unit 202 may provide treatment control such as stabilization of the treatment parameters including power, frequency, impedance, temperature of the device, temperature of the energy delivery element, and/or temperature of the treated tissue. Central control unit 202 may include a flex circuit and/or printed circuit board. Central control unit 202 may include a microprocessor and memory.

Energy generator 203 may generate and/or regulate one or more types of energy applied during the treatment. In addition, energy generator 203 may generate and/or regulate one type of energy generating another type of energy, for example light generating laser light.

In one embodiment, energy generator 203 may comprise a high frequency energy generator and transmatch adjusting the input impedance to the impedance of the treated tissue in order to maximize the power transfer. The high frequency generator may be connected to a balun transformer.

In another embodiment, energy generator 203 may comprise an ultrasound energy generator. The ultrasound energy generator may include an ultrasound transducer, backing material, coupling liquid, and an acoustic window. An ultrasound energy generator may include at least one lens. An ultrasound transducer may be a piezoelectric transducer or capacitive transducer. The length of the ultrasound transducer may be in the range of 1 mm to 500 cm or 1.5 mm to 50 cm or 1.5 mm to 25 cm. The volume of the ultrasound transducer may be in the range of 1 $mm^3$ to 800 $cm^3$ or 1.5 $mm^3$ to 600 $cm^3$ or 2 $mm^3$ to 400 $cm^3$. The energy generator generating ultrasound may be located in the applicator.

In another embodiment, an energy generator may comprise a light emitting diode, a laser emitting diode, an optical fiber, a flashlamp or any light source known in the art.

Sensor 204 may provide information about at least one physical quantity and its measurement may lead to feedback. Sensor 204 may provide information about at least one physical quantity including energy, output of at least one energy delivery element, impedance of the tissue and/or energy delivery element, temperature of the treated tissue, temperature of the untreated tissue, temperature of the energy delivery element, temperature of the lens, temperature of at least one layer of the tissue, water content of the device, phase angle of delivered and/or reflected energy, position of the device, position of the applicator, temperature of the cooling media and/or temperature of the energy generator. Sensor 204 may be a temperature, acoustic, vibration, electric, magnetic, flow, positional, optical, imaging, pressure, force, energy flux, impedance, current, Hall and/or proximity sensor. The sensor 204 may be a capacitive displacement sensor, acoustic proximity sensor, gyroscope, accelerometer, magnetometer, infrared camera and/or thermographic camera. The sensor may be located on the applicator and/or in the case. For example, a temperature sensor may be located on the applicator, while the impedance sensor may be located in the case. One sensor may measure more than one physical quantity. For example, the sensor 204 may include a combination of a gyroscope, an accelerometer and/or a magnetometer.

The device may include a temperature sensor located on the applicator and/or the tip. The temperature sensor may include an IR sensor, a thermocouple and the like. The method of treatment may include measurement of the temperature of tissue, treated tissue, temperature of at least one layer of the tissue and/or untreated tissue. In addition, the method of treatment may include measurement of temperature of one or more energy delivery elements. When the temperature of the tissue is above a predetermined interval or value, a central control unit and/or a device may provide a human perceptible signal and/or change one or more parameters of the treatment.

The device may include an imaging sensor used for imaging of a tissue region. The method of treatment may include imaging a tissue region before treatment and after treatment to compare the state of the tissue region and measure and/or detect the treatment effect and/or treatment action. Also, the method of treatment may include imaging of a treated tissue region and an untreated tissue region to measure and/or detect the treatment effect and/or treatment action. The imaging sensor may be a camera, infrared camera or ultraviolet camera. The temperature sensitivity of the infrared camera may be better than 0.1 K or 0.5 K. The infrared camera may be located on the applicator and/or tip. The imaging sensor may be located on the applicator and may provide continual measurement during movement of the applicator. The imaging sensor may be used for creating a temperature distribution map, which may be shown on the user interface 205, case user interface 209 and/or applicator user interface 214. A temperature distribution map may include information about the temperature of the surface of the tissue and/or at least one subsurface layer of the tissue. Also, the user may use the infrared camera to obtain an image of the treated body part and/or tissue area. After that, the user may evaluate homogeneity of the heating and eventually use the device for additional treatment of the tissue. The camera and/or central control unit may determine whether the body part which should be treated again with the same type of energy and same parameters, with the same type of energy and different parameters and/or with a different type of energy.

The device may include a position sensor unit including an accelerometer, magnetometer and/or gyroscope. Such a sensor unit may be an inertial measurement unit. Methods of treatment may include detection of position, speed or angle of the applicator in the vicinity and/or on the surface of the tissue. In one example, the position sensor unit may detect an intentional and/or unintentional stop of the continuous movement of the applicator. In such cases, the device may provide feedback represented by changing at least one parameter of the treatment and/or by a human perceptible signal preventing damage (e.g. burning) of the tissue. In another example, the position sensor unit may detect and/or measure the speed of continuous movement. The central control unit may compare the data obtained from the position sensor unit with one or more predetermined values of recommended speed. When the measured speed of the applicator differs from the recommended speed e.g. by 5%, 10% or 20%, the device may provide a human perceptible signal and/or change at least one parameter of the treatment. In another variation, the central control unit may compare the data obtained from a position sensor unit with one or more predetermined intervals of recommended speed. When the measured speed of the applicator is out of the said intervals, the device may provide a human perceptible signal and/or change at least one parameter of the treatment. In still another example, the position sensor unit may measure the angle of the applicator and/or tip to the tissue, estimating the quality of contact between the tip and tissue. When the angle is outside of a predetermined range, the device may provide a human perceptible signal. In still another example, the position sensor unit may detect the pathway of the continuous movement of the applicator. Such information may be used for generation of a movement map on the user interface, comparison of treatment duration and treatment completion of different body parts, and/or generation of information about an untreated tissue area which the user considers as already treated.

The device may include an impedance sensor which may be used for detecting and evaluating contact of the applicator with tissue. When the impedance sensor detects insufficient contact with the tissue, the device may provide a human perceptible signal and/or change at least one parameter of the treatment. Such feedback may prevent tissue injury including burning of tissue. In one embodiment, the device may decrease the power output of radiofrequency energy and/or ultrasound energy.

The human perceptible signal may include sound, change of applicator color, change of tip color, change of color of the user interface and/or visual representation of a possible correction on the user interface. Changes of treatment parameters may include changes of power, frequency, duration, spot size, wavelength, current and/or voltage of one or more types of energy. Changes of at least one parameter may therefore include ceasing treatment. In one embodiment, the change of treatment may include lowering the power output, or ceasing of delivery of one or all types of energy.

User interface 205 provides the operator the ability to operate and control the device and method of treatment. User interface 205 may be integrated into part of the device, e.g. the case or applicator. In some embodiments, there may be one user interface built into the applicator and a second user interface built into the case. User interface 205 may include a control panel including a display, buttons, touchpad, keyboard or other control members. The display may provide information about a process and/or a result of treatment and/or imaging. The display may also provide information about a sensed physical quantity. Additionally, the user interface may include at least one external device e.g. a laptop, PC, mobile phone and/or tablet. The user interface 205 may be connected to a feedback unit (e.g. vibration unit), which may provide haptic feedback (e.g. vibration) when the operator uses the user interface 205.

Energy delivery element 206 may include at least one electrode, acoustic window, optical window or other energy delivery element known in the art. The electrode may be an RF electrode. The RF electrode may be a dielectric electrode coated with insulating material. In one embodiment, the RF electrode positioned on the surface of the applicator may act as an acoustic window for ultrasound energy. The RF electrode may be a part of a tip of the applicator. The RF electrode may have a surface area in the range of 0.01 cm$^2$ to 250 cm$^2$ or 0.1 cm$^2$ to 150 cm$^2$ or 0.2 cm$^2$ to 100 cm$^2$. The energy delivery element 206 may be in direct contact, indirect contact or in contact with the treated tissue. In the case of direct contact, the energy delivery element 206 directly contacts the surface of the tissue. In the case of indirect contact, there is a gap between the tissue and energy delivery element 206, wherein the gap is filled by one or more spacing objects. Spacing objects may include foam, a bolus filled with fluid, or textile. In case of no contact, the energy delivery element 206 may be spaced from the tissue by a gap, wherein the gap is filled by air.

Figure 3A:
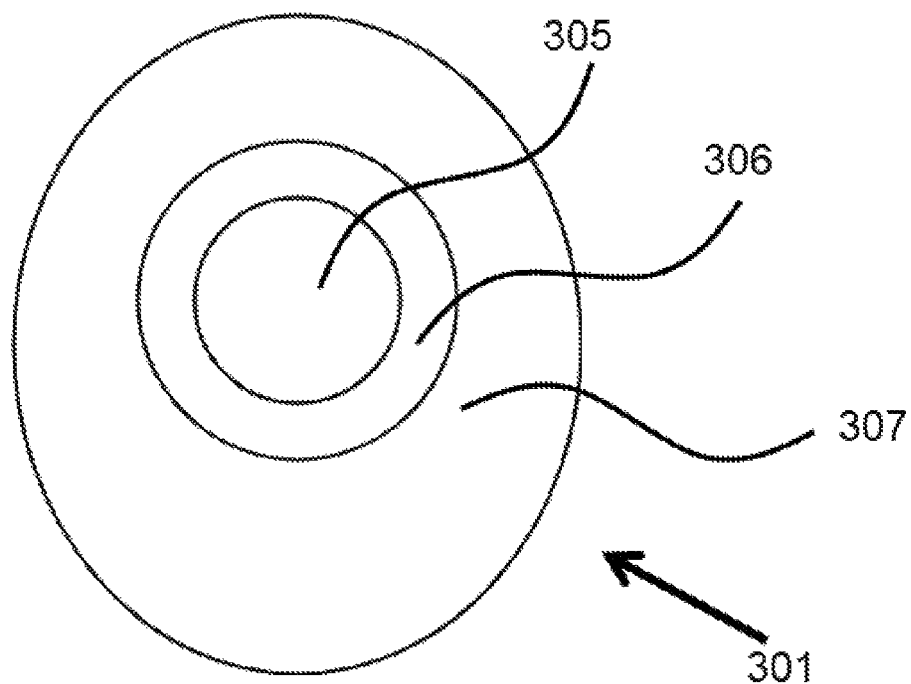
FIG. 3A is a frontal view of an exemplary tip.

The applicator 208 may include a replaceable tip including an RF electrode, ultrasound energy generator, acoustic window and/or sensor. FIG. 3A shows a frontal view of exemplary tip 301 of the applicator including acoustic window 305 and RF electrode 306. The RF electrode 306 and/or acoustic window 305 may be in direct contact with the skin, preferably without penetration of surface of the skin. The acoustic windows 305 may transfer the mechanical stimulation to the skin of the patient. The acoustic windows may be surrounded by the RF electrode. The energy delivery elements may be positioned on the applicator as a set of concentric circles. The acoustic window in form of the circle may have a diameter in the range of 1 mm to 200 mm or 5 mm to 60 mm or 10 mm to 30 mm. The surface area of the acoustic window may be in the range of 0.1 cm$^2$ to 300 cm$^2$ or 0.5 cm$^2$ to 150 cm$^2$ or 1 cm$^2$ to 50 cm$^2$. The surface area of the RF electrode being in contact with the tissue may be in the range of 0.25 cm$^2$ to 100 cm$^2$ or 0.3 cm$^2$ to 50 cm$^2$ or 0.5 cm$^2$ to 35 cm$^2$. The ratio between the surface area of the RF electrode and the surface area of the acoustic window (cm$^2$/cm$^2$) may be in the range of 0.001 and 1000 or 0.01 to 100 or 0.05 to 50 or 0.25 to 25.

Figure 3B:
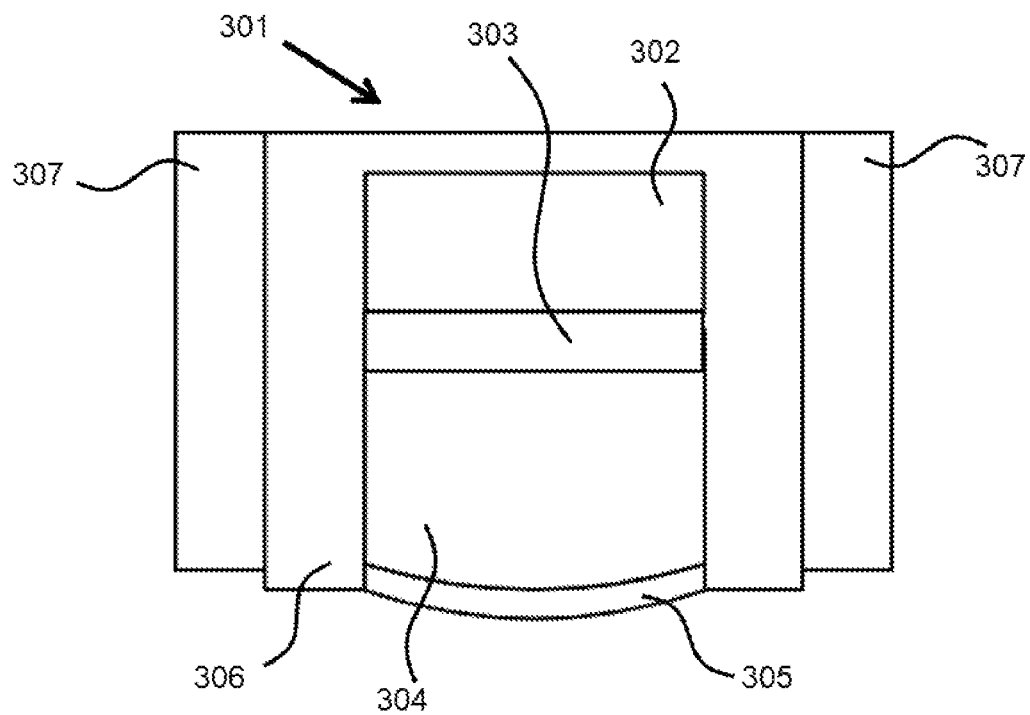
FIG. 3B is an exemplary embodiment of a tip.

In one embodiment, the RF electrode and acoustic window are distinct parts of the applicator. FIG. 3B shows exemplary tip 301 of the applicator. Tip 301 includes ultrasound transducer 302, lens 303, cavity 304, acoustic window 305, RF electrode 306 and casing 307. The ultrasound transducer 302 may be positioned above lens 303 and above cavity 304 including fluid. Fluid in cavity 304 may be paraffin oil, ricin oil, water or water mixed with alcohol. In addition, the cavity 304 may be filled by plastic e.g. silicone or polyurethane. Cavity 304 includes an acoustic window 305 on the side facing the tissue. Ultrasound energy may be transferred to tissue also without presence of a lens. Acoustic window 305 may be made from any material including a polyimide membrane, e.g. Kapton. The material of the acoustic window 305 may have an acoustic impedance in the range of 0.01 MRayl to 500 MRayl or 0.05 MRayl to 250 MRayl or 0.1 MRayl to 150 MRayl. Tip 301 further includes at least one RF electrode 306. Acoustic window 305 and RF electrode 306 act as energy delivery elements. The acoustic window 305 may be convex or concave. Also, as shown on FIG. 3B, the acoustic windows 305 may form a bulge above the line formed by the RF electrode. In another embodiment, the acoustic window 305 may form a recess below the line formed by the RF electrode.

Figure 3C:
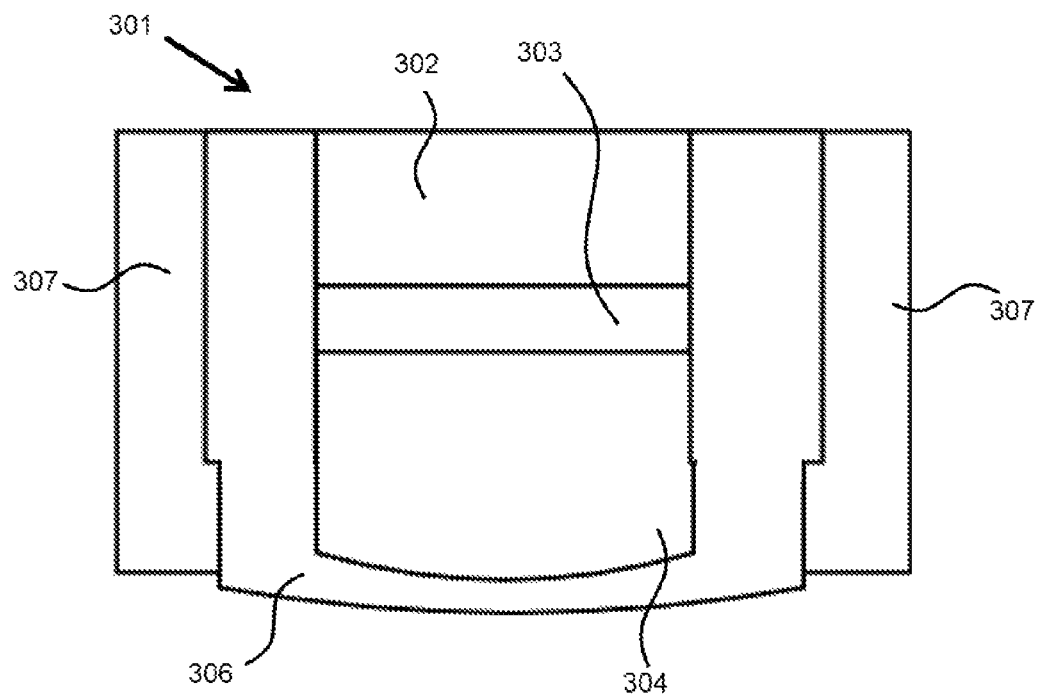
FIG. 3C is another exemplary embodiment of a tip.

In another embodiment, the RF electrode 306 may act as an acoustic window. FIG. 3C shows another exemplary tip 301 including ultrasound transducer 302, lens 303, cavity 304, RF electrode 306 and casing 307. Ultrasound energy may be transferred to tissue without the presence of lens 303. The RF electrode 306 is encasing the cavity 304 and acts as an acoustic window.

Figure 3D:
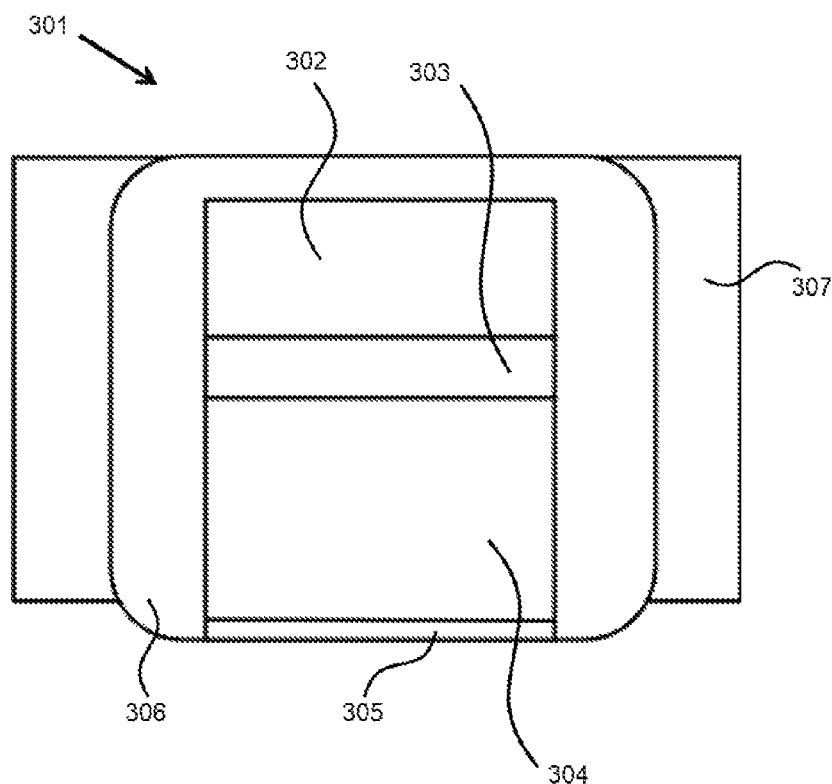
FIG. 3D is another exemplary embodiment of a tip.

FIG. 3D shows still another exemplary embodiment of another exemplary tip 301, wherein the RF electrode 306 and acoustic window 305 are distinct parts of an exemplary tip. In this embodiment, the RF electrode 306 and acoustic window 305 may form a linear front in contact with the tissue.

Figure 3E:
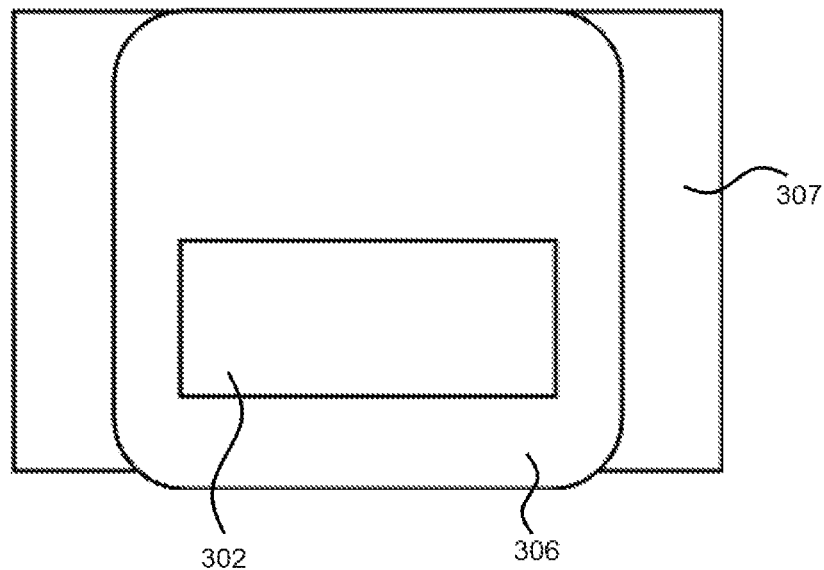
FIG. 3E is another exemplary embodiment of a tip.
Figure 3F:
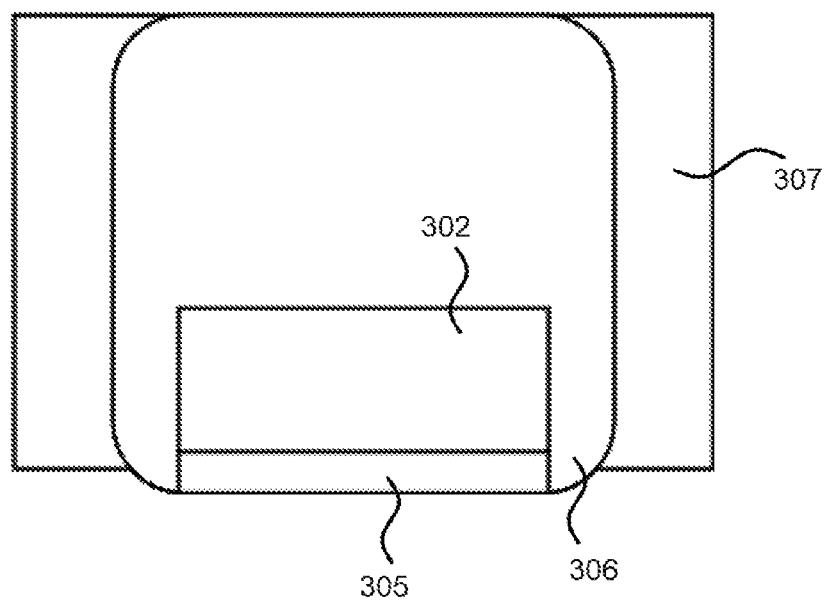
FIG. 3F is another exemplary embodiment of a tip.

FIG. 3E shows still another exemplary embodiment of another exemplary tip without any cavity. The RF electrode 306 acts as an acoustic window. The applicator may not include a lens. FIG. 3F shows still another exemplary embodiment of a tip without any cavity but with an acoustic window 305. The ultrasound transducer 302 may be positioned above the acoustic window 305 or at a certain distance from the acoustic window 305. The distance between the lower surface of the ultrasound transducer 302 and surface of the acoustic window in contact with the tissue may be in a range of 0.1 cm to 20 cm or 0.15 cm to 15 cm or 0.15 cm to 10 cm.

Figure 4:
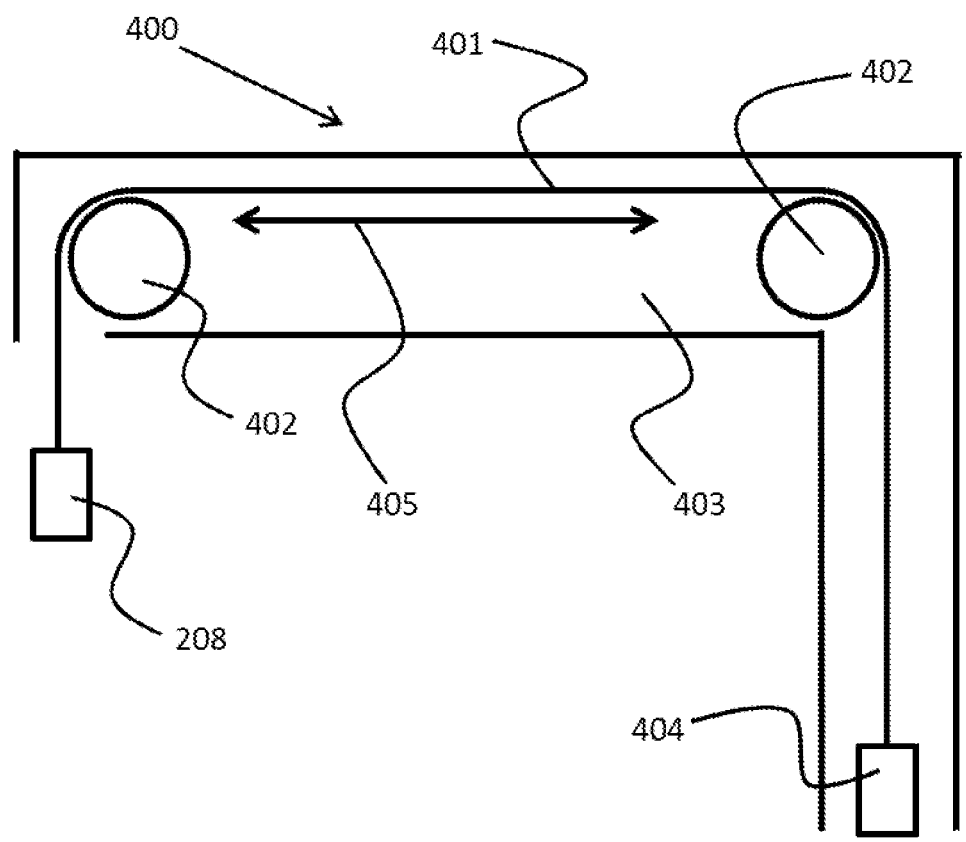
FIG. 4 is an exemplary embodiment of a positioning element.

FIG. 4 shows an exemplary embodiment of a positioning element 400 which may ease operation of the device by reducing fatigue of the user. The positing apparatus may include one or more links 401, sheaves 402 and/or counterweight elements 404. Link 401 and sheaves 402 may be located in the guiding channel 403. Link 401 may be flexible. Link 401 (e.g. rope) may be moved in the direction of the arrow 405. Counterweight element 404 may compensate for the weight of the applicator 208. Forward movement of the link 601 may increase the pressure applied by the applicator 208 on the tissue. Backward movement of the link may be enhanced by counterweight element 404. Methods of treatment may include a combination of forward and backward movements in order to provide sufficient pressure of the applicator on the tissue.

Figure 5:
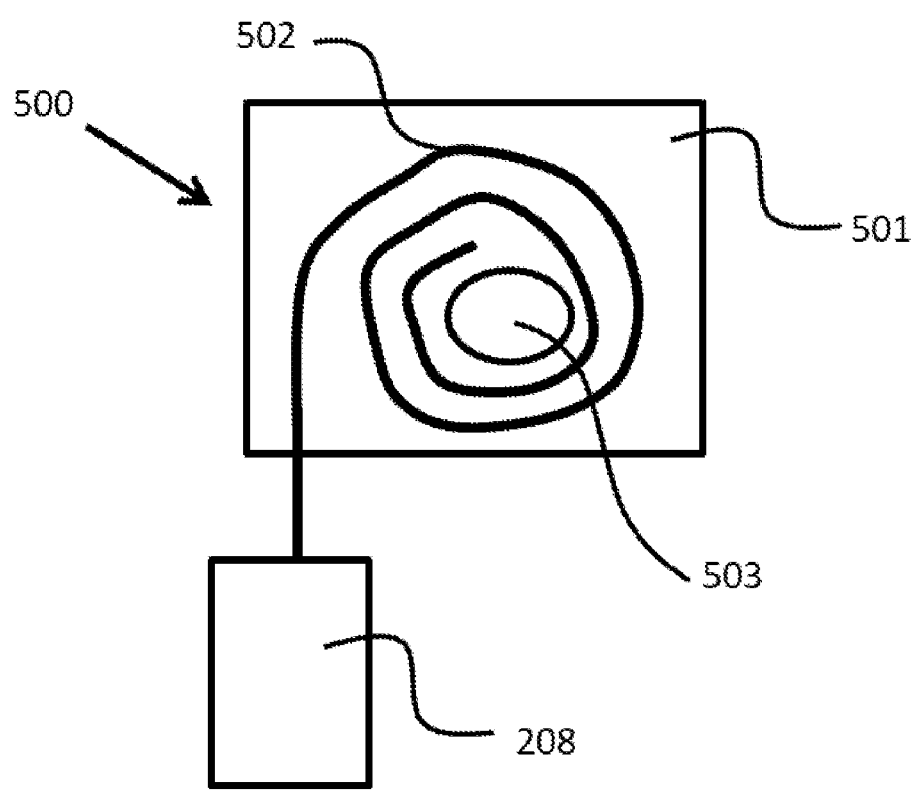
FIG. 5 is another exemplary embodiment of a positioning element.

FIG. 5 shows another exemplary embodiment of a positioning element. The shown positioning element 500 includes link 502 and rolling member 501, which may be enclosed in casing 501. During methods of treatment, link 502 may be reeled out when the user presses the applicator 208 downwards. Also, the link may be reeled in, when the user does not press the applicator 208 downward, therefore the reeling in force provides compensation for the weight of the applicator 208. Casing 501 may be part of a guiding arm having at least one degree of freedom.

Methods of treatment may include the following steps: preparation of the tissue, positioning of the applicator adjacent to the tissue; application of the energy; and movement of the applicator. More than one step may be executed in one moment, e.g. movement of the applicator and application of the energy.

Preparation of the tissue may include application of a transfer medium (e.g. ultrasound gel) and/or a pharmaceutical composition to the tissue. Pharmaceutical compositions may include an anesthetic agent providing local anesthesia. Such pharmaceutical agents may be lidocaine, benzocaine, procaine, prilocaine and/or a mixture of at least two agents, such as a mixture of lidocaine and prilocaine or a mixture of lidocaine and tetracaine or a mixture of tetracaine together with cocaine and adrenaline. Pharmaceutical agents may be provided topically or in an injection.

Positioning of the device may include positioning at least one applicator providing one or more types of energy adjacent to a tissue of the patient. In one embodiment, positioning of the device may include positioning the applicator in contact with tissue or the surface of the tissue of the patient in a noninvasive manner, i.e. without penetrating or piercing the patient's tissue, skin, tissue surface and/or skin surface. In one embodiment, positioning of the device may include positioning the applicator providing ultrasound energy and radiofrequency energy in contact with a surface of the tissue or surface of the skin of the patient.

Application of the energy may include providing at least one type of energy from an applicator into a tissue. Application of energy may include providing of at least two types of energy from one or two energy delivery elements. In one embodiment, application of the energy to the tissue may include providing radiofrequency energy and ultrasound energy from the applicator into the skin of the patient and providing one or more treatment actions to the tissue of the patient. In such cases, energy delivery elements providing radiofrequency energy may be capacitive or resistive RF electrodes. Ultrasound energy may be provided through an acoustic window.

Application of the energy may be coupled with influencing the cells to enhance, renew or improve biosynthesis of at least one component of an extracellular matrix. Cells may be influenced during treatment and/or after treatment. Influence may last for a prolonged period of time.

Movement of the applicator may include movement of the applicator adjacent to treated tissue. In one embodiment, movement of the applicator may include continuous movement of the applicator in contact with and/or on the surface of the tissue, e.g. skin. In another embodiment, movement of the applicator may include lifting the applicator from the tissue area after application of the energy and contacting tissue on another treatment site. The one or more types of energy may be applied during movement of the applicator.

In one embodiment a treatment may include treatment of the abdomen. The applicator may be positioned and moved in contact with the surface of tissue between sulcus intermammarius and mons pubis or rib cage and iliac crest.

In another embodiment a treatment may include treatment of the triceps. The applicator may be positioned in contact with and moved with the surface of tissue between the shoulder and elbow or axilla and olecranon.

In another embodiment a treatment may include treatment of the biceps. The applicator may be positioned and moved in contact with the surface of tissue between shoulder and elbow or shoulder joint and elbow pit.

In another embodiment a treatment may include treatment of a forearm. The applicator may be positioned and moved in contact with the surface of tissue between the elbow and wrist or antecubital fossa and rascette line of wrist or olecranon and styloid process of radius/ulna.

In another embodiment a treatment may include treatment of a hand. The applicator may be positioned and moved in contact with the surface of tissue between the wrist and finger nails or rascette line of the wrist and finger nails.

In another embodiment a treatment may include treatment of the inner thighs. The applicator may be positioned and moved in contact with the surface of tissue between the mons pubis and knee or mons pubis and popliteal fossa.

In another embodiment a treatment may include treatment of a banana roll of the leg. The applicator may be positioned and moved in contact with the surface of tissue between the gluteal fold and the knee or the gluteal fold and the popliteal fossa.

In another embodiment a treatment may include treatment of the back. The applicator may be positioned and moved in contact with the surface of tissue between the sacral triangle and the neck.

In another embodiment a treatment may include treatment of one or both buttocks. The applicator may be positioned and moved in contact with the surface of tissue between the sacral triangle and the gluteal fold.

In another embodiment a treatment may include treatment of the love handles. The applicator may be positioned and moved in contact with the surface of tissue between the armpit and the gluteal fold or rib cage and greater trochanter of femur.

In another embodiment a treatment may include treatment of the saddle bags. The applicator may be positioned and moved in contact with the surface of tissue between armpit and gluteal fold or iliac crest and knee joint.

In another embodiment a treatment may include treatment of the neck. The applicator may be positioned and moved in contact with the surface of tissue between fifth pair of ribs and mental protuberance of chin.

In another embodiment a treatment may include treatment of the forehead. The applicator may be positioned and moved in contact with the surface of tissue above the frontalis, depressor supercilii, corrugator supercilii, procerus and/or orbicularis oculi muscles.

In another embodiment a treatment may include treatment of eyelids. The applicator may be positioned and moved in contact with the surface of tissue above the orbicularis oculi muscles.

In another embodiment a treatment may include treatment of the perioral area. The applicator may be positioned and moved in contact with the surface of tissue above the depressor labii inferioris, genioglossus, mentalis and/or orbicularis oris muscles.

In another embodiment a treatment may include treatment of the lips. The applicator may be positioned and moved in contact with the surface of tissue above, orbicularis oris muscles.

In another embodiment a treatment may include treatment of one or both breasts. The applicator may be positioned and moved in contact with the surface of tissue above the Cooper's ligaments.

In another embodiment a treatment may include treatment of the upper cheeks. The applicator may be positioned and moved in contact with the surface of tissue above orbicularis oculi, levator labii superioris, zygomaticus minor, zygomaticus major and/or masseter.

In another embodiment a treatment may include treatment of the lower cheeks. The applicator may be positioned and moved in contact with the surface of tissue above the masseter, risorius, depressor anguli oris, stylohyoid, zygomaticus minor, zygomaticus major and/or platysma.

In another embodiment a treatment may include treatment of the tissue above the pectoralis major. The applicator may be positioned and moved in contact with the surface of tissue above the pectoralis major.

Methods of treatment may include application and use of a neutral electrode adjacent to a treated body part. The neutral electrode may be part of the applicator or be separate from the applicator. The neutral electrode may be applied to the tissue before the application of energy. Typically, the neutral electrode may be applied as an adhesive electrode. When the neutral electrode is applied to the tissue, the device may measure the resistance of the neutral electrode. In one embodiment, the device may measure and save the lowest resistance value of the neutral electrode, which may be obtained after application of the full surface of the electrode on the skin. The resistance value may then be measured during the treatment and application of energy and be compared to the lowest resistance value measured during the same or previous treatment. When the measured resistance value of the neutral electrode deviates from the lowest resistance value, the device may provide a human perceptible signal, and/or change at least one parameter of the treatment. The deviation of the resistance value of the neutral electrode may occur for example when the neutral electrode becomes detached from the tissue. Measuring the resistance value of neutral electrode and responsive feedback may prevent damage to the tissue and pain during treatment. In another embodiment, the device may measure the highest resistance value of the neutral electrode, which may be measured before adhesion of the neutral electrode to the tissue. Also, the resistance value of the neutral electrode may be compared to a value set by the central control unit before treatment. The lowest deviation of the resistance value leading to feedback may be 1%, 5%, 10%, 15% or 20%.

The methods of treatment and devices may also be used for treatment of tissue with injected or inserted hyaluronic acid dermal fillers to provide them sufficient deposition into the skin. In case of fillers, the term "hyaluronic acid" may include biologically acceptable preparations of hyaluronic acid, including crosslinked products or soluble salts. A combination of radiofrequency energy and ultrasound energy may provide more homogenous deposition of hyaluronic acid from the dermal fillers.

Thus, novel apparatus and methods have been shown and described. Various changes and substitutions may of course be made without departing from the spirit and scope of the invention. The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The invention, therefore, should not be limited except by the following claims and their equivalents.

The invention claimed is:

1. A method for enhancement, renewing or improvement of biosynthesis of hyaluronic acid in a skin of a patient comprising:
    positioning at least one applicator in contact with the skin of the patient;
    providing a first type of energy via at least one radiofrequency electrode driven by a central control unit, providing a heating having an energy flux on the surface of the skin in a range of 0.001 $W/cm^2$ to 1500 $W/cm^2$ and an output power of less than or equal to 250 W, wherein the radiofrequency electrode is a dielectric electrode coated with insulating material and having a surface area in a range of 0.01 $cm^2$ to 250 $cm^2$;
    providing a second type of energy providing a targeted heating and having an energy flux on the surface of the skin in a range of 0.001 $W/cm^2$ to 250 $W/cm^2$ and an output power of less than or equal to 20 W;
    applying the first and second types of energy to a reticular dermis and/or an epidermal basal layer;
    heating the reticular dermis and/or the epidermal basal layer to a temperature in a range of 35° C. to 65° C.; and
    stimulating the skin to enhance, renew or improve biosynthesis of hyaluronic acid; and
    obtaining a temperature of one or more energy delivering elements from a temperature sensor located in the applicator.

2. The method according to claim 1 wherein the targeted heating is provided to a target area; and
    wherein a temperature of the target area is increased up to 15° C. higher than a temperature of a tissue outside of the target area affected by the first type of energy.

3. The method according to claim 2 wherein the target area has a volume in a range of 0.1 $mm^3$ to 1400 $mm^3$.

4. The method according to claim 3 wherein the targeted heating is applied to a degree sufficient to cause proliferation of fibroblasts.

5. The method according to claim 4 wherein the target area does not comprise the surface of the skin.

6. The method according to claim 5 wherein the applicator is positioned in contact with a tissue without penetrating a surface of the skin.

7. The method according to claim 6 further comprising application of the first and second types of energy sufficient to cause increased proteosynthesis of at least one hyaluronan synthase.

8. The method according to claim 6 further comprising application of the first and second types of energy sufficient to cause increased production of or synthesizing a precursor of hyaluronic acid.

9. A method for enhancement, renewing or improvement of biosynthesis of hyaluronic acid in a skin of a patient comprising:
  providing a first type energy providing a non-targeted vibrational movement of at least one cell and having an energy flux on the surface of the skin in a range of 0.001 W/cm$^2$ to 1500 W/cm$^2$ and an output power less than or equal to 250 W;
  providing a second type of energy providing a heating having an energy flux on the surface of the skin in a range of 0.001 W/cm$^2$ to 250 W/cm$^2$ and an output power less than or equal to 20 W;
  wherein the first and second types of energy are applied to reticular dermis and/or epidermal basal layer; and
  heating the reticular dermis and/or the epidermal basal layer to a temperature in a range of 35° C. to 65° C.;
  wherein both types of energies are provided from a replaceable tip of an applicator in contact with the skin of the patient, the replaceable tip including at least one of a radiofrequency electrode, ultrasound energy generator, acoustic window, or sensor; and
  stimulating the skin to enhance, renew or improve biosynthesis of hyaluronic acid.

10. The method according to claim 9 wherein the applicator does not penetrate the surface of the skin.

11. The method according to claim 10 wherein the second type of energy is an ultrasound energy provided through an acoustic window, wherein the surface of the acoustic window has an area in a range of 0.01 cm$^2$ to 300 cm$^2$.

12. The method according to claim 11 wherein the first type of energy is radiofrequency energy and the combined energy flux of the radiofrequency energy and the ultrasound energy is in a range of 0.002 W/cm$^2$ to 1750 W/cm$^2$.

13. The method according to claim 12 wherein a ratio of a frequency of the radiofrequency energy to a frequency of the ultrasound energy (MHz/MHz) is in a range of 0.0001 to 5000.

14. The method according to claim 13 wherein a beam non-uniformity ratio of the ultrasound energy is less than 15.

15. The method according to claim 13 wherein a ratio between the output power of the ultrasound energy on the surface of the applicator to the output power of the ultrasound energy on the surface of the acoustic window (W/cm$^2$) is in a range of 0.001 to 1500.

16. A method for enhancement, renewing or improvement of biosynthesis of hyaluronic acid in a skin of a patient comprising:
  positioning at least one applicator in contact with the skin of the patient;
  providing a radiofrequency energy via at least one radiofrequency electrode driven by a central control unit, which is providing a treatment action and having a frequency in a range of 350 kHz to 100 MHz, output power on the surface of the skin less than or equal to 250 W, energy flux in a range of 0.001 W/cm$^2$ to 1500 W/cm$^2$, and surface area of the electrode in a range of 0.01 cm$^2$ to 250 cm$^2$, wherein the radiofrequency electrode is a dielectric electrode coated with insulating material;
  providing a second type of energy providing a targeted treatment action;
  wherein both treatment actions are applied to a reticular dermis and/or an epidermal basal layer; and
  heating the reticular dermis and/or the epidermal basal layer to a temperature in a range of 35° C. to 65° C.;
  stimulating the skin to enhance, renew or improve biosynthesis of hyaluronic acid;
  wherein both treatment actions cause proliferation of fibroblasts; and
  wherein the applicator includes an applicator user interface configured to inform the user about at least one therapy parameter.

17. The method according to claim 16 wherein the second type of energy is ultrasound energy having a frequency in a range of 100 kHz to 100 MHz, output power on the surface of a tissue of less than or equal to 20 W, an energy flux on the surface of the applicator in a range of 0.001 W/cm$^2$ to 250 W/cm$^2$, a beam non-uniformity ratio less than 15, and a treatment depth in a range of 0.2 mm to 50 mm.

18. The method according to claim 17 wherein the ratio between the output power of the ultrasound energy on the surface of the applicator and the output power of the ultrasound energy on the surface of the acoustic window (W/cm$^2$) is in the range of 0.001 to 1500.

19. The method according to claim 18 wherein a temperature of a surface of the skin is increased to a value in a range of 37° C. to 55° C.

20. The method according to claim 17 wherein the radiofrequency energy and the ultrasound energy are applied simultaneously for a time period in a range of 0.01 to 300 seconds.

21. The method according to claim 18 wherein a combined energy flux of radiofrequency energy and ultrasound energy on the surface of the tissue is in a range of 0.002 W/cm$^2$ to 1750 W/cm$^2$.

22. A method according to claim 21 wherein the applicator does not penetrate the surface of the skin.

* * * * *